| United States Patent [19] | [11] Patent Number: 4,876,089 |
| Luciw et al. | [45] Date of Patent: Oct. 24, 1989 |

[54] FELINE LEUKEMIA VIRUS PROTEIN VACCINES

[75] Inventors: Paul Luciw, Emeryville; Deborah L. Parkes, Oakland; Gary A. Van Nest, El Sobrante, all of Calif.

[73] Assignee: Chiron Corporation, Emeryville, Calif.

[21] Appl. No.: 87,954

[22] Filed: Aug. 14, 1987

Related U.S. Application Data

[63] Continuation of Ser. No. 647,966, Sep. 6, 1984, abandoned.

[51] Int. Cl.[4] .............................................. A61K 37/02
[52] U.S. Cl. .................................. 424/89; 530/350; 530/403; 530/806; 935/65
[58] Field of Search .................... 424/89; 935/65; 530/350, 403, 806

[56] References Cited

U.S. PATENT DOCUMENTS

| 3,966,907 | 6/1976 | Jarrett et al. | 424/89 |
| 4,034,081 | 7/1977 | Jarrett et al. | 424/89 |
| 4,086,134 | 4/1978 | Jarrett et al. | 424/89 |
| 4,117,112 | 9/1978 | Jarrett et al. | 424/89 |
| 4,264,587 | 4/1981 | Pederson et al. | 424/89 |
| 4,332,793 | 6/1982 | Olsen | 424/89 |
| 4,434,157 | 2/1984 | Olsen | 424/89 |
| 4,663,436 | 5/1987 | Elder et al. | 530/324 |
| 4,701,416 | 10/1987 | Nunberg | 435/320 |
| 4,722,840 | 2/1988 | Valenzuela et al. | 424/88 |

FOREIGN PATENT DOCUMENTS

WO85/02625 6/1985 World Int. Prop. O. ............ 424/88

OTHER PUBLICATIONS

Hunsmann et al., Virology, 113:602–612 (1981).
Salerno et al., J. Nat'l Cancer Inst., vol. 61, No. 6, pp. 1487–1493 (1978).
Lewis et al., Infection and Immunity, 34:888–894 (1981).
Pinter et al., Virology, 83:417–422 (1977).
Pinter et al., Virology, 91:345–351 (1978).
Lewis et al., *Infection and Immunity*, (1981) 34:888–894.
Hunsmann et al., *Virology*, (1981) 113:602–612.
Salerno et al., *Natl. Cancer Inst.*, (1978) 61:1487–1493.

*Primary Examiner*—Christine M. Nucker
*Attorney, Agent, or Firm*—Spencer & Frank

[57] ABSTRACT

Methods and compositions are provided for the efficient production of a polypeptide having immunological reactivity corresponding to that of naturally-occurring envelope glycoproteins of feline leukemia virus. A DNA construct including a replication system recognized by yeast, and a viral envelope protein gene under the transcriptional control of a yeast promoter, and terminator is provided. By transforming a yeast host with the DNA construct, enhanced yields of the product may be obtained.

*Saccharomyces carlsbergensis* strains 2150-2-3 (pCP-envB-R) and 2150-2-3 (pCP-envA-R) were deposited at the American Type Culture Collection on July 18, 1984, and granted accession nos. 20720 and 20721, respectively.

13 Claims, 4 Drawing Sheets

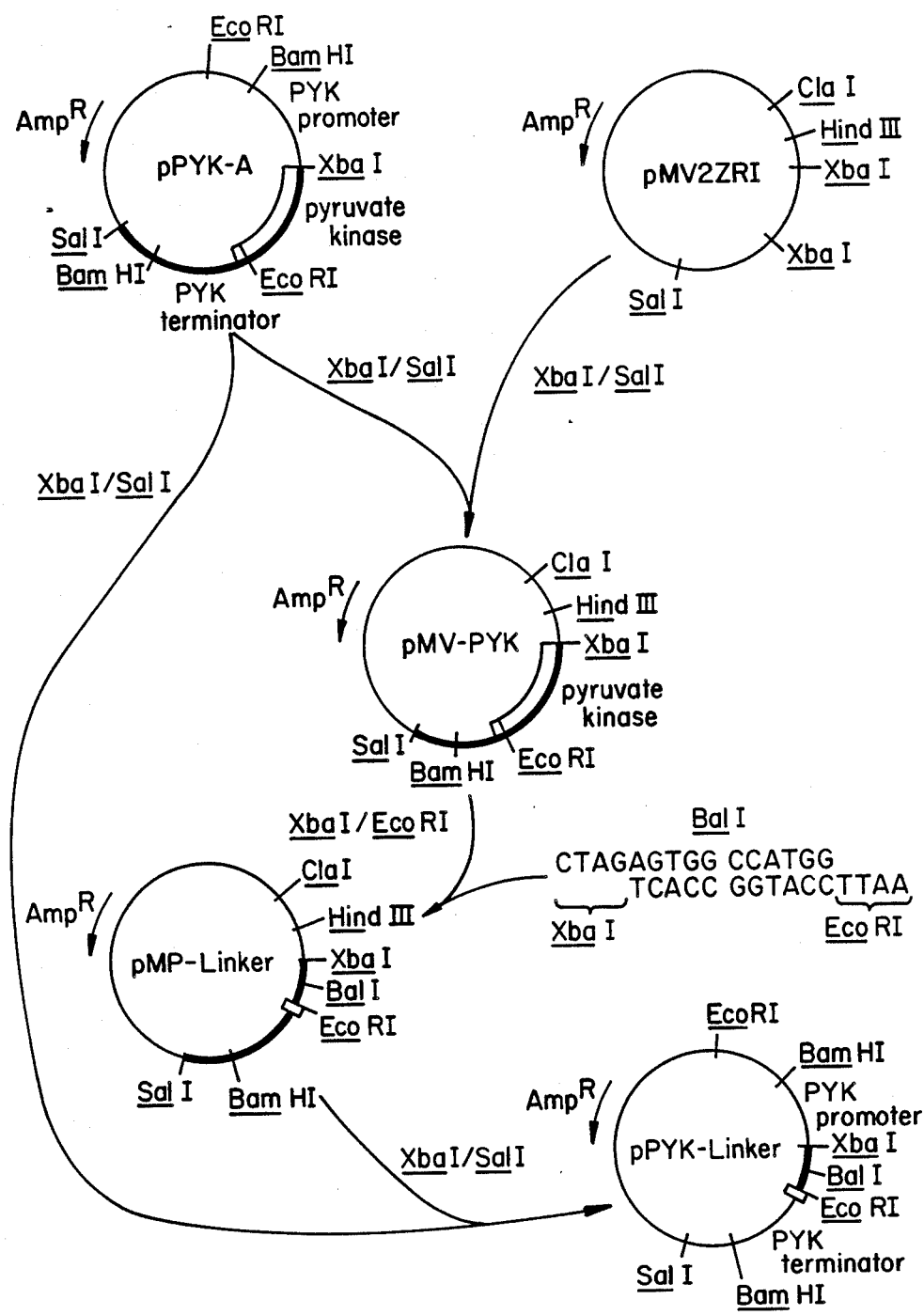
FIG._1A.

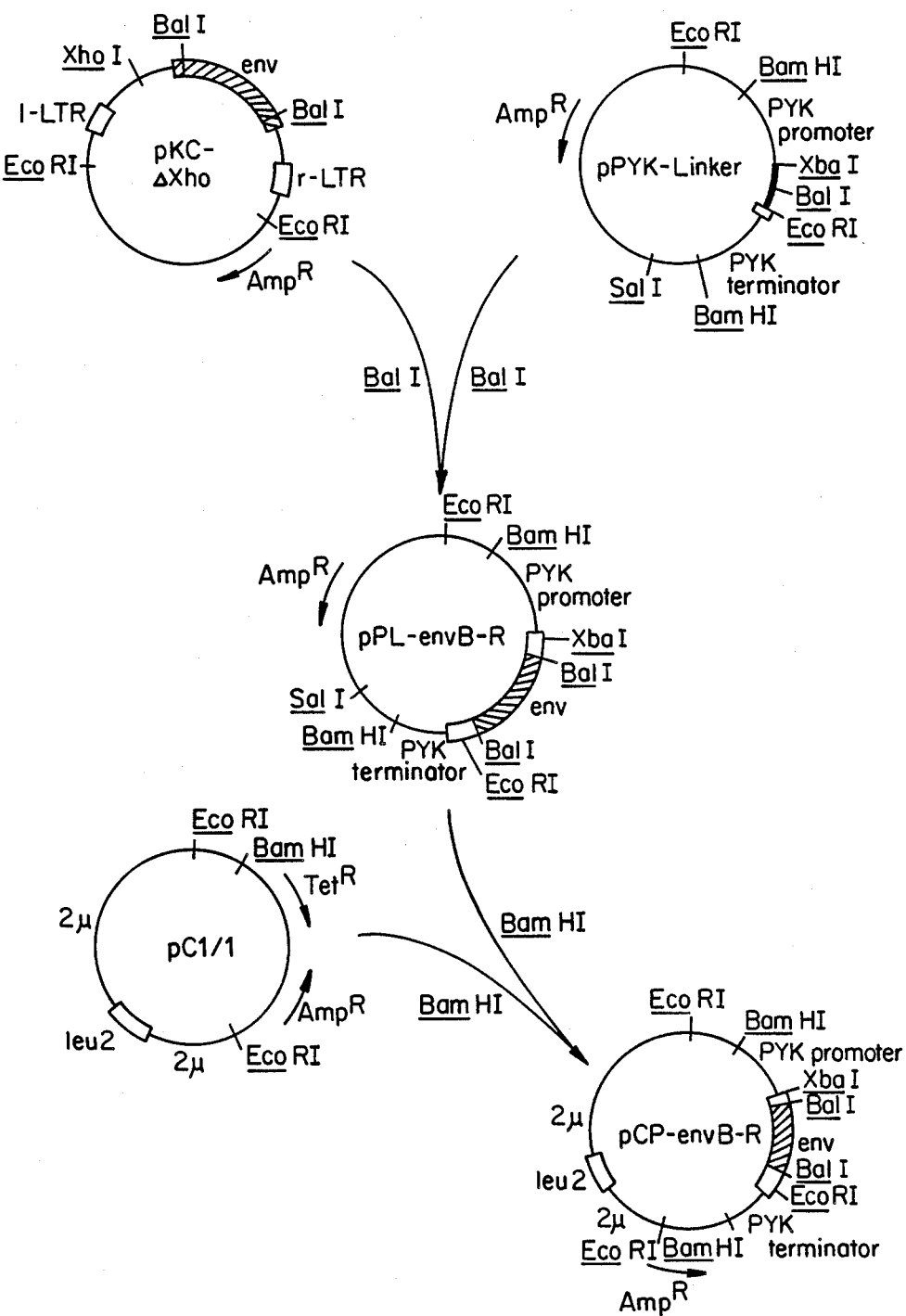
FIG._1B.

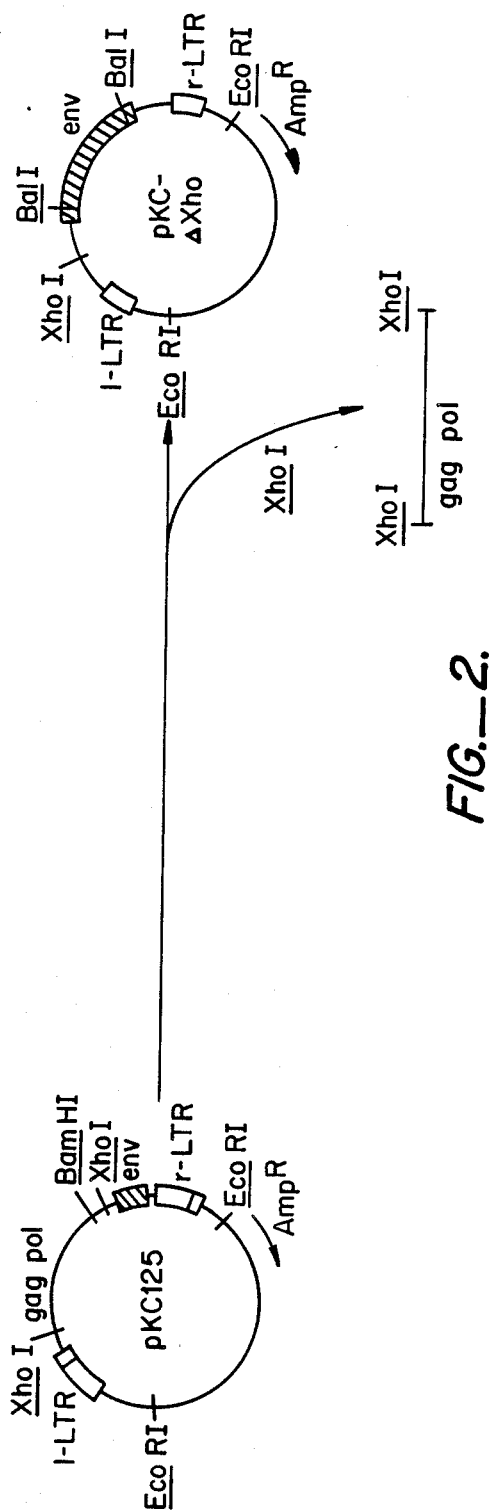
FIG._2.
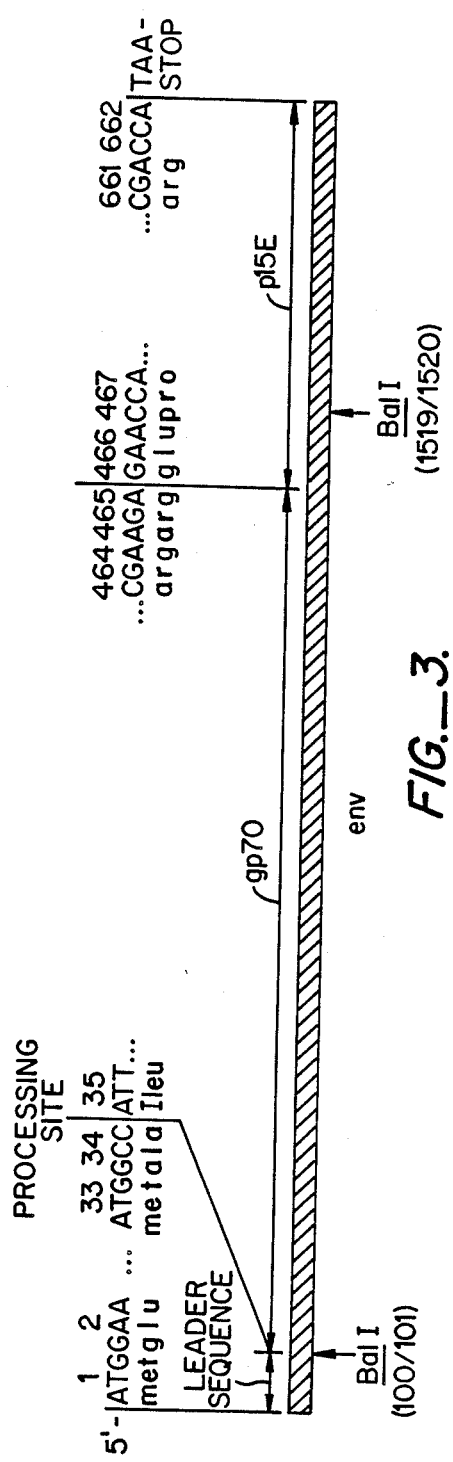
FIG._3.

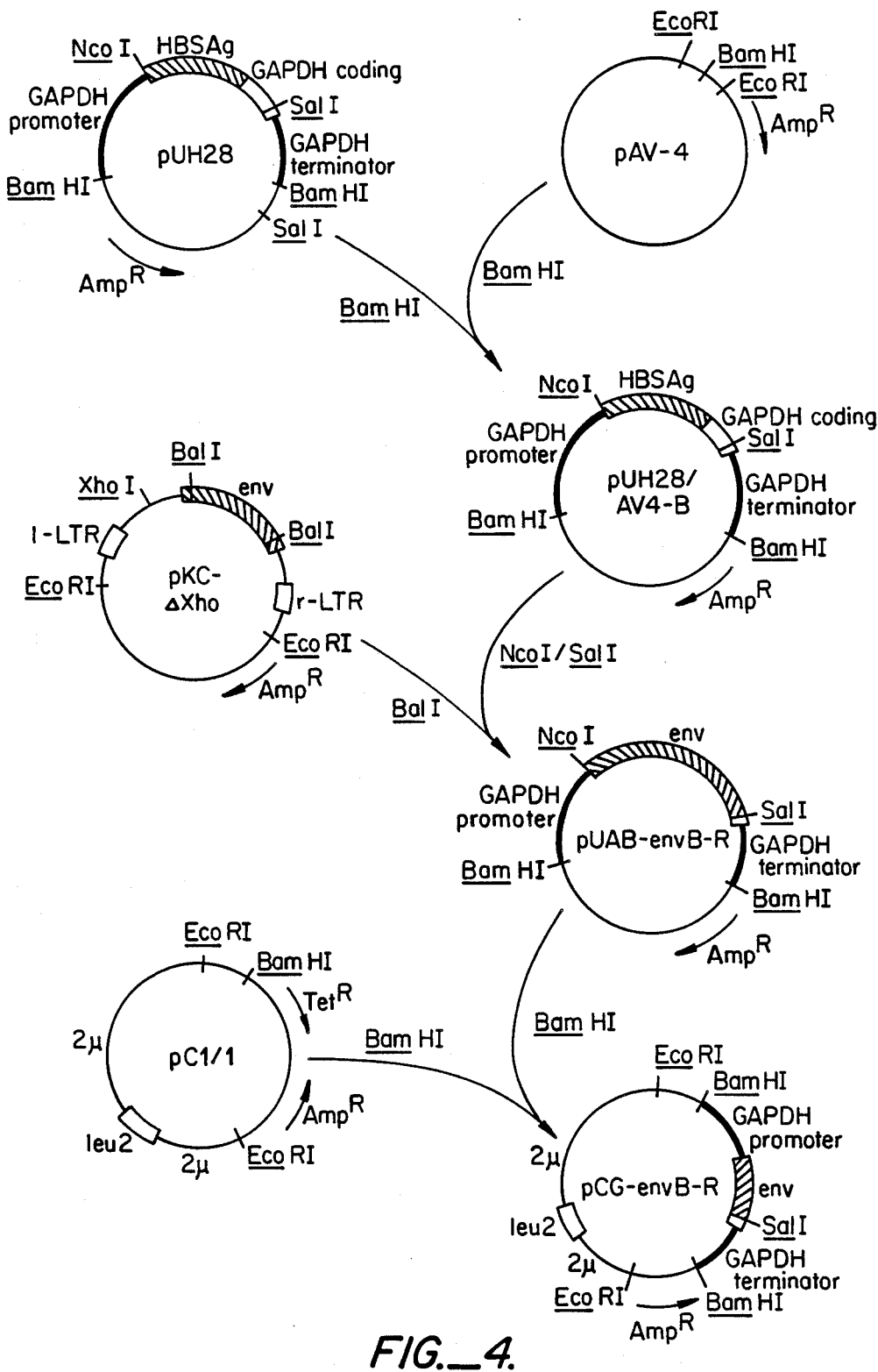
FIG._4.

FELINE LEUKEMIA VIRUS PROTEIN VACCINES

This application is a continuation of application Ser. No. 647,966 filed Sept. 6, 1984, abandoned.

BACKGROUND OF THE INVENTION

1. Field of the Invention Feline leukemia virus (FeLV) is a retrovirus having three subgroups designated A, B and C. FeLV is highly infectious among cats and is responsible for a number of diseases including lymphosarcomas, leukemias, thymic lymphomas, fibrosarcomas (with helper-dependent feline sarcoma virus), and non-regenerative anemias. FeLV infection in cats also causes suppression of the immune system which exposes the animal to opportunistic infection by a variety of pathogens.

A variety of vaccines against FeLV infection have been prepared, including attenuated live virus, killed virus, killed virus-infected cells, vaccines based on FeLV-tumor cell antigens, and vaccines based on viral envelope glycoproteins. None of these attempts have been wholly successful. The envelope glycoproteins utilized for vaccination were isolated from purified virus. Because of the difficulty in purification, only limited testing was performed and the dosages of the glycoproteins were low. The inoculated cats developed low levels of both precipitating antibodies and cytotoxic antibodies, and very low levels of neutralizing antibodies.

It would thus be desirable to provide a safe, reliable, and economic vaccine which provides effective protection against FeLV infection. It would be particularly desirable to provide relatively large quantities of FeLV envelope protein from a source other than the virus itself, which could additionally serve as a commercial supply for diagnostic assays.

2. Description of the Prior Art

Salerno et al., J. Natl. Cancer Inst. (1978) 6:1487-1493 have reported the use of an envelope glycoprotein isolated from purified FeLV as a vaccine. Hunsmann et al., Virology (1981) 113:602-612 have reported envelope glycoprotein acquire immunity to viral challenge. Lewis et al., Infection and Immunity (1981) 34:888-894, have described the use of a FeLV vaccine made of soluble tumor cell antigen. The use of glyceraldehyde-3-phosphate and pyruvate kinase promoters for gene expression in eukaryotic hosts is described in copending application Ser. No. 468,589, filed Feb. 22, 1983, in the names of Burke et al., the description of which is incorporated herein by reference.

SUMMARY OF THE INVENTION

Polypeptides having immunological activity analogous to that of feline leukemia virus (FeLV) envelope glycoproteins are efficiently produced utilizing an expression vector comprising a DNA sequence encoding the primary structure of an FeLV envelope glycoprotein under transcriptional control of a promoter recognized by a microorganism expression host. In the exemplary embodiment, coding sequences are obtained from proviral DNA, and the promoters are derived from yeast glycolytic enzymes, e.g., glyceraldehyde-3-phosphate dehydrogenase (GAPDH) and pyruvate kinase (PYK). The polypeptides of the present invention are useful as substitutes for the naturally-occurring FeLV envelope glycoproteins, particularly as an immunologically active substance in vaccines for FeLV or as a detection reagent for FeLV in diagnostic assays.

BRIEF DESCRIPTION OF THE DRAWINGS

FIGS. 1A and 1B are flow diagrams depicting the preparation of plasmid pCP-envB-R.

FIG. 2 is a flow diagram depicting the preparation of pKC-ΔXho carrying the FeLV-B envelope glycoprotein gene from pKC125.

FIG. 3 illustrates the FeLV-B envelope gene (env) shown with the coding strand in the 5′ to 3′ direction. The env gene fragment includes a first BalI restriction site between nucleotides 100 and 101 in the leader sequence, and a second BalI restriction site between nucleotides 1519 and 1520 in the p15E region.

FIG. 4 is a flow diagram depicting the preparation of plasmid pCG-envB-R.

DESCRIPTION OF THE SPECIFIC EMBODIMENTS

Methods and compositions are provided for the efficient expression of polypeptides demonstrating immunological activity analogous to that of FeLV envelope glycoproteins. By analogous immunological activity, it is meant that, when administered to a vertebrate, the polypeptides elicit an immunological response which is similar to that elicited by administration of the natural glycoproteins, e.g., cross-reactive neutralizing antibodies are produced.

The methods employ a DNA construct including a sequence encoding the polypeptide joined to a transcriptional promoter recognized by a preselected microorganism host, usually yeast. The DNA construct frequently includes a replication system recognized by the host to form an extrachromosomal element, and may include other sequences, such as a secretory leader and processing signal, a prokaryotic replication system, selective markers, and the like. By introducing the DNA construct into the preselected microorganism host, the desired polypeptide can be expressed and isolated.

Feline leukemia virus is an RNA retrovirus. The proviral form of FeLV is integrated into the host genome and includes an approximately 8.8 kbp coding region flanked at either end by identical long terminal repeat (LTR) sequences which are 485 base pairs in length. Transcription of the coding sequence is controlled by the 5′-LTR, while polyadenylation of the resulting transcript is controlled by the 3′-LTR. The coding sequence includes the leader, gag, pol, and envelope (env) regions. The gag and pol regions encode for certain core proteins, while the env region encodes a polyprotein which is cleaved yielding two envelope proteins designated gp70 and p15E. Glycoprotein gp70 has a molecular weight of approximately 70 kilodaltons (kd). Differences in the gp70 region appear to account for the different subgroups, i.e., A, B and C.

In accordance with this invention DNA sequences are provided which include a fragment of a gp70 sequence which DNA sequences encode for a polypeptide which is a gp70 cross-reactive immunogen. By cross-reactive in the present context is intended that the immunogen has an epitope which specifically binds to an antibody which binds to at least one gp70 of one of the FeLV subgroups. The polypeptides will be unglycosylated or glycosylated in accordance with the glycosylation system of the microorganism host so as to be glycosylated in other than the naturally occurring manner. Despite the differences in glycosylation, the subject polypeptides do cross-react with antibodies to the naturally occurring gp70.

Thus, the polypeptides expressed from the DNA constructions of the subject invention will include polypeptides comprising at least one immunogenic sequence of gp70, gp70, gp70 joined to part or all of p15E, the env expression product, a fused polypeptide having the gp70 epitopic sites specific for 2 or 3 of the FeLV subgroups, or any of these fused to a polypeptide of from 10 to 200 amino acids which polypeptide is alien or foreign to FeLV.

Hereinafter, unless specified otherwise, the phrase "FeLV envelope gene" intends the DNA sequence coding for at least an immunogenic portion of gp70 specific for at least one subgroup of FeLV.

According to the present invention, a FeLV envelope protein gene is obtained and expressed in a suitable microorganism host. The FeLV envelope gene is a double stranded (ds) DNA fragment which encodes for at least a portion of the amino acid sequence of the FeLV envelope glycoprotein of interest. The nucleotide sequence of the gene will usually be substantially identical to the naturally-occurring sequence from which it was derived, although some deviation is acceptable so long as the polypeptide product retains the immunological activity of the natural glycoprotein.

Conveniently, the proviral dsDNA form of FeLV can be isolated and cloned, although it is also possible to employ cDNA obtained directly from the viral RNA. Proviral DNA is obtained by restriction digestion and gradient fractionation of the genomic DNA from an FeLV infected mammalian cell line. Fractions containing fragments of suitable length, usually about 8 to 25 kbp, may be identified and concentrated by ethanol precipitation. These fragments may be cloned in a suitable cloning vector, and recombinant clones carrying the FeLV DNA identified using a suitable probe. Such probes may employ RNA obtained from FeLV itself, or DNA or RNA obtained from related viruses, such as the murine leukemia virus, which displays substantial homology with FeLV RNA. Alternatively, the probes may employ synthetic DNA based on the FeLV envelope gene sequences set forth hereinafter.

In addition to the coding sequence for the FeLV envelope protein of interest, the DNA constructs of the present invention will include at least a promoter which is recognized by the microorganism host. The microorganism host will usually be yeast, although other microorganism capable of appropriate expression of the gene product will also be suitable.

A wide variety of suitble promoters are available from yeast. Promoters of particular interest include those promoters involved with enzymes in the glycolytic pathway, such as the promoters for alcohol dehydrogenase, glyceraldehyde-3-phosphate dehydrogenase, pyruvate kinase, triose phosphate isomerase, phosphoglucoisomerase, phosphofructokinase, and the like. Particularly preferred are the inducible promoters of glyceraldehyde-3-phosphate dehydrogenase and pyruvate kinase. For example, when yeast cultures are shifted from growth on acetate to glucose, the activity of glyceraldehyde-3-phosphate dehydrogenase is increased up to 200 fold. By isolating these promoters with their naturally-occurring flanking regions including transcriptional regulatory sequences, such as enhancers, operators, etc., and using a host having an intact regulatory system, one can regulate the transcription and expression of the FeLV envelope gene by properly controlling the nutrient medium.

The DNA construct will usually include a terminator proximate to the 3'-end of the FeLV envelope gene. Although it may not be necessary for expression, the provision of a terminator enhances expression of the gene. Conveniently, the terminator can be the terminator which is naturally associated with the promoter. When a different terminator is used, it should be selected to be balanced, i.e., a strong promoter should have a strong terminator and a weak promoter should have a weak terminator. Strong promoters and terminators are preferred since they provide for increased expression of the FeLV envelope gene.

To form an extrachromosomal element, the DNA construct will be provided with a replication system capable of providing for stable, extrachromosomal replication in the host of interest. Both bacterial and yeast hosts will be of use, although yeast hosts are preferable for expression. Yeast hosts may allow for post-translational modification, e.g., glycosylation, which may increase the immunological similarity between the polypeptide product of the present invention and naturally-occurring FeLV envelope glycoproteins.

A number of suitable yeast replication systems are reported by Botstein et al. (1979) Gene 8:17-24. of particular interest are the YEp plasmids which contain the 2 $\mu$m plasmid replication system. The 2 $\mu$m replication system can provide for stable maintenance of multiple copies of the plasmid in yeast. Alternatively, a combination of ARS1 and CEN4 may be utilized. When used for cloning of the DNA construct, the replication system will usually be bacterial. Suitable bacterial replication systems are well known and widely reported in the patent and scientific literature. Often, it will be desirable to employ a shuttle vector having both yeast and prokaryotic replication systems to allow for cloning and expansion of the DNA construct in a prokaryotic host and expression of the product in yeast.

In addition to th FeLV envelope gene, promoter, terminator, translation regulatory sequences and replication systems, the DNA construct may be provided with one or more regions which facilitate identification of transformants, regulate replication of the plasmid, or regulate expression of the FeLV envelope gene. For example, the DNA construct will usually be provided with markers which allow for selection of transformants. Conveniently, genes may be provided for biocide resistance, such as antibiotic resistance or heavy metal resistance. Alternatively, a gene expressing a particular metabolite will allow for selection of transformants in an auxotrophic host.

Other capabilities may also be introduced into the DNA construct. For example, sequences homologous to a host chromosome may be provided for integration into the host genome. Genes may then be included in the construct which are amplifiable. Upon integration into the genome, genes are amplified in response to stress to the host. By placing such amplifiable genes upstream from the promoter, coding sequence and other signals regulating expression of the env gene, and stressing the host, multicopy genes may be obtained with a plurality of tandem repeating sequences capable of expressing the polypeptide(s) of interest. Illustrative amplifiable genes include metallothioneins and dihydrofolate reductase.

Additionally, certain temperature-sensitive regulatory regions allow for modulation of transcription by varying the temperature. Thus, by introducing such a sequence a suitable distance upstream from the promoter, and growing the microorganism host at a "nonpermissive" temperature which lessens transcription, one can grow the cells to high density before utilizing the cell to produce the product of interest. After high density has been achieved, the temperature can be adjusted to provide for maximum expression of the polypeptide. Useful temperature-sensitive regulatory regions may be obtained from the genes coding for heat-shock proteins found widely in prokaryotes and eukaryotes.

Often, it will be desirable to join the FeLV envelope gene to secretory leader and processing signals to provide for secretion and processing of the envelope glycoprotein. Various secretory leaders and processing signal sequences have been described in the scientific and patent literature. See, for example, U.S. Pat. Nos. 336,336, 338,397 and 411,994 as well as copending applications Ser. Nos. 522,909, filed Aug. 12, 1983, and 488,857, filed Apr. 26, 1983, the relevant portions of which are incorporated herein by reference.

In preparing the DNA constructs of the present invention, it will usually be necessary to join the various individual DNA sequences described above together in a predetermined order. Since the sequences are derived from diverse sources, it will often be convenient or necessary to join the sequences by means of connecting or adaptor molecules. Such adaptor molecules are short synthetic dsDNA fragments, typically having cohesive ends selected to join to the ends of the DNA sequences derived from natural sources. The nucleotide sequence of the synthetic linkers can be chosen to regenerate portions of the natural DNA sequence which were excised when the sequences were obtained by restriction from larger fragments. Additionally, the linkers can be utilized to introduce new restriction sites at desired locations in the DNA construct, and the length of the linking fragment can be selected to assure that the individual DNA sequences are properly spaced apart.

Methodology for manipulating individual DNA constructs is amply described in texts such as Maniatis et al. "Molecular Cloning" (1982) Cold Spring Harbor Laboratory. Generally, two DNA sequences of interest are joined in vitro using techniques such as homopolymer tailing, annealing of cohesive ends, blunt end ligation, linkers, or the like. By providing selective markers on one or both of the sequences, recombinant molecules combining both sequences in the proper order can be identified. Further screening or scoring using DNA/RNA probes may also find use. After the desired recombinant molecule is identified, the molecule can be cloned in a convenient host, usually prokaryotic, to expand the number of recombinant molecules. Multicopy plasmids, amplifiable genes, and the like, are useful at this stage. After the host carrying the recombinant molecule is grown out, the recombinant molecule may be isolated and used as a source of DNA for the next step in preparing the DNA construct. These manipulations may be repeated as many times as necessary until all the DNA sequences have been joined in the proper order.

In preparing the exemplary DNA constructs described in the Experimental section hereinafter, advantage was taken of preexisting vectors, one of which included the promoter and terminator derived from pyruvate kinase (plasmid pPYK-A) and another of which included the promoter and terminator derived from glyceraldehyde-3-phosphate dehydrogenase (plasmid pUH28). A third preexisting plasmid (pKC125, pFeA12ΔXS or pFeClAΔXS) carrying the entire env gene locus (including both gp70 and p15E, see FIG. 3) from FeLV(-B, A or C, respectively) was also utilized. As described in detail in the Experimental section, a portion of the envelope gene encoding the gp70 glycoprotein was inserted between the pyruvate kinase promoter (including a portion of the pyruvate kinase coding sequence) and terminator in pPYK-A, and the resulting fragment carrying the promoter, the FeLV envelope gene including a complete gp70 sequence and partial p15E sequence and terminator, in proper order, was inserted into yeast plasmid pCl/l to provide pCP-envA, B or C. Similarly, the same FeLV gene sequence as above encoding for gp70 was inserted between the GAPDH promoter and terminator on pUH28, and the resulting fragment carrying the promoter, gp70 gene and terminator, in proper order, was then inserted into plasmid pCl/l to form pCG-envB.

The plasmids of the present invention may be introduced into the yeast host by any convenient means, employing whole cells or spheroplasts, and using polyethylene glycol precipitated DNA for transformation, or liposomes, or other conventional techniques. The modified hosts may be selected based on the genetic markers which are provided. For example, plasmids carrying a gene which complements an auxotrophic host, may be selected based on prototrophy of the auxotrophic host. Alternatively, resistance to a biocide may be selected for by providing the biocide in the culture medium. The cells containing the plasmid may then be grown in an appropriate nutrient medium, and the desired polypeptide isolated using conventional techniques. The desired polypeptide may be purified by chromatography, filtration, extraction, or the like. Conveniently, when the polypeptide is secreted into the medium, the nutrient medium may be recycled by continuously removing the envelope glycoprotein.

The subject polypeptides find use as vaccines. Hosts may be inoculated by any convenient means with a sufficient amount of the polypeptide to provide an immune response. The amount of polypeptide will generally be from about 1 $\mu g$ to 20 mg/kg host, usually from about 5 $\mu g$ to 2 mg/kg host, although this figure may vary depending on the type of administration, frequency of administration, and the like. The glycoprotein may be in any convenient physiologically acceptable medium, for example, sterile water, phosphate buffered saline, growth medium, or the like with or without adjuvant Usually, the total dosage volume will be about 0.5 to 2.0 ml. Administration will be by injection, either subcutaneously, intramuscularly, intraperitoneally, or the like. Booster injections will be employed as necessary. Immunization with glycoprotein from each of the three strains, A, B and C of FeLV may be utilized or alternatively a combination of two or all of them.

A method was developed for purifying aqueous insoluble polypeptides retained in the cytoplasm of unicellular microorganism cells, particularly yeast cells. (By insoluble is intended no significant dissolution in not more than five volumes of water, pH 8.0, at room temperature.) The cell wall is removed in conventional ways to prepare spheroplasts or protoplasts. The resulting cells are isolated and washed with a substantially isotonic solution, e.g., 1 M orbitol, followed by osmotic lysis with a buffered (about pH 7.5–8.5) hypotonic saline solution (~5–30 mM) containing protease inhibitors, e.g., phenylmethylsulfonyl fluoride, pepstatin, etc. at conventional concentrations. The insoluble material is isolated and washed in 0.5–2 volumes (based on approximate insoluble material volume) of an aqueous surfactant solution, e.g., 0.1–0.3% alkyl (10–16 carbon atoms) sulfate, e.g., sodium dodecyl sulfate, containing conventional protease inhibitors. The washing proceeds for at least one hour, usually at least about six hours and generally does not require more than 24 hours. The temperature will be about −5 to 10° C. The purified insoluble polypeptide may then be isolated by conventional ways, e.g., centrifugation. Polypeptide compositions of at least 50% purity, usually at least about 70% purity, can be isolated in their native form without denaturation.

The polypeptides produced by the subject invention can also be used as reagents in diagnostic assays. Conveniently, the polypeptides may be labeled with labels such as radionuclides, fluorescers, enzymes, particles, or the like, where the labels provide, either directly or indirectly, a detectable signal, and employed in conventional procedures for the determination of the presence of antibodies to gp70 or gp70 in physiological fluids. The polypeptides may also be used as immunogens for the production of antibodies which may be used for passive immunization, as reagents in diagnostic assays or for other conventional uses.

The following examples are offered by way of illustration and not by way of limitation.

EXPERIMENTAL

Unless otherwise indicated, all percentages are by weight and all temperatures are in celsius. The following abbreviations are used:

Amp$^R$—ampicillin resistant
ATP—adenosine triphosphate
CAA—casamino acids
DMSO—dimethyl sulfoxide
DTT—dithiothreitol
LSB—Laemmli protein gel sample buffer
STC—1 M sorbitol, 10 mM CaCl$_2$, 10 mM Tris (pH 7.5)
TE—10 mM Tris, 1 mM EDTA
PBS—phosphate saline buffer
PEG—polyethylene glycol
SDS—sodium dodecyl sulphate
tet$^R$—tetracycline resistant
dNTP—dATP, dCTP, dGTP or dTTP

Materials and Methods

1. Plasmids used in the construction of yeast expression vectors for envelope protein of FeLV-A, FeLV-B or FeLV-C. ps (a) Plasmids containing DNA coding for the envelope protein of FeLV-A, FeLV-B or FeLV-C.

(i) Plasmid pKC125 (FIG. 2):

The DNA sequence coding for the envelope protein of FeLV-B was obtained from plasmid pKC125 (obtained from Dr. James Casey, Louisiana State University). This plasmid was obtained by subcloning a 10 Kb EcoRI fragment containing the complete genome of FeLV-B into a 2.2 kb pBR322 derivative which has deletion comprising the tet$^R$ gene. The EcoRI fragment was obtained from a clone λHF60 from a lambda library constructed as described in Mullins et al., J. of Virol. (1981) 38:688–703.

(ii) Plasmid pFeA12ΔXS:

This plasmid was derived from pFeA12A (described below) and contains part of the FeLV-A provirus including all the coding region for the envelope protein.

To construct pFeA12ΔXS, a XhoI (site in the provirus sequence) - SalI (site in the vector sequence) deletion was made. To obtain this deletion pFeA12A was digested with XhoI and with SalI. The plasmid was self-ligated and cloned in HB101 to produce pFeA12ΔXS.

(iii) Plasmid pFeC1AΔXS:

This plasmid was derived from pFeC1A (described below) and contains part of the FeLV-C provirus including all the coding region for the envelope protein. To construct pFeC1AΔXS, plasmid pFeC1A was digested with XhoI and SalI. The plasmid was self-ligated to produce pFeC1AΔXS.

(iv) Plasmids pFeA12A and pFeC1A were constructed as follows (see copending application, Ser. No. 93,339, filed 3/26/84):

High molecular weight whole cell DNA from the human RD-4 cell lines infected with FeLV-A or FeLV-C was prepared by phenol-chloroform extraction and a sample of each digested with various restriction endonucleases. The restricted DNA was analyzed by Southern blotting with a $^{32}$P-radiolabeled probe specific to FeLV sequences corresponding to a BssHI fragment of FeLV-B DNA which comprises almost the entire proviral genome since this enzyme cleaves twice in each LTR only. EcoRI restrictions sites were not detected in the proviral DNA in either cell line; therefore, the whole cell DNA preparations isolated from each were digested to completion with EcoRI, centrifuged in sucrose gradients and fractions corresponding to 8–15 kb were pooled, dialyzed and concentrated by ethanol precipitation. The bacteriophage derivative cloning vector, EMBL-4 (see Karn et al., Methods Enzymol. (1983) 101:3–19) was digested to completion with a mixture of EcoRI, BamHI and SalI restriction enzymes and the DNA then deproteinized by phenol-chloroform extraction, precipitated with cold ethanol and resuspended in ligation buffer. (The brief alcohol precipitation selectively recovers large DNA fragments (e.g., phage arms) while the small linker DNA is retained in solution; SalI/SalI filler fragments are not incorporated into the construct during subsequent ligation.) The EMBL-4 phage DNA and EcoRI digest of cellular DNA are mixed and ligated, and the resultant recombinant phage genomes packaged in vitro. After phage infection of λ-sensitive E. coli, phage plaques were transferred to nitrocellulose filters, DNA was fixed and the filters were screened with FeLV-specific radiolabeled probe as above. Positive plaques, consisting of phage containing the entire FeLV-A or C proviral DNAs, together with flanking human (RD-4 cell) DNA, were recovered. Plasmid pFeA12A or pFeC1A were then obtained by subcloning the provirus FeLV-A or FeLV-C respectively, from EMBL-4 into pBR328. FeLV-A provirus was inserted into the SstI/EcoRI site of the cam$^R$ gene with resulting plasmid being cam$^S$, amp$^R$, and tet$^R$. FeLV-C provirus was inserted into the EcoRI site of the cam$^R$ gene with the resulting plasmid being cam$^S$, amp$^R$ and tet$^R$.

(b) Plasmids containing glyceraldehyde-3-dehydrogenase (GAPDH) or pyruvate kinase (PYK) promoter and terminator sequences.

(i) Plasmid pUH28 (FIG. 4):

Plasmid pUH28 contains the coding and 3' non-coding regions of the Hepatitis B surface antigen (HBsAg) gene fused in incorrect reading frame to the first 7 codons of the yeast GAPDH structural gene. This fusion is flanked at its 5' end by the GAPDH promoter and its 3' end by part of the GAPDH coding region followed by the GAPDH terminator. This plasmid was constructed so as to have an NcoI site at the 3' end of the first 7 codons of the GAPDH gene with the following sequence:

The SalI site used in the preparation of the yeast vector containing FeLV sequences is at the 5' region of the GAPDH terminator. Therefore, by digesting pUH28 with NcoI and partially with SalI a deletion of the HBsAg coding plus non-coding regions and of the GAPDH coding region is obtained.

The construction of pUH28 involves cloning of a fragment that contains the HBsAg coding and 607 bp of 3' non-coding region prepared from pHBS5-3 Hae2-1 (described below) into the GAPDH containing vector pGAP'$_2$ (described below). To prepare the fragment, pHBS5-3 Hae2-1 was linearized by PstI digestion, partially digested with NcoI and a PstI-NcoI fragment of 1.9 Kb containing pBR322 sequences, HBsAg coding and 3' sequences was purified by gel electrophoresis. This fragment was subsequently digested with EcoRI and a 1.2 Kb NcoI-EcoRI fragment containing the HBsAg coding and 3' non-coding regions was purified by gel electrophoresis. Plasmid pGAP'$_2$ was linearized with XbaI and treated with Bal31 to remove approximately 100 bp total. The plasmid was subsequently digested with NcoI and a vector fragment of about 8 Kb was purified by gel electrophoresis. The NcoI ends of the vector and the 1.2 Kb NcoI-EcoRI fragment encoding HBsAg were ligated. The recessed ends were filled in with Klenow and the resulting blunt ends were ligated to the blunt end of the vector obtained by Bal31 digestion to produce pUH28.

pHBS5-3 Hae2-1 is a plasmid that contains the HBsAg coding region and 607 bp of the 3' flanking sequence. This plasmid is a derivative of pHBS5-3 which contains the same insert but only 128 bp of 3' untranslated region instead of 607 bp Plasmid pHBS5-3 has been previously described in copending application, Ser. No. 609,540, filed May 11, 1984 (pp. 13-14). pHBS5-3 Hea2-1 was constructed as follows. The HBV genome (3.2 kb) was excised from pHB-3200 (Valenzuela et al., Nature (1979) 280:815-819) by restriction digestion with EcoRI. The 3.2 kb fragment was purified by gel electrophoresis and was recircularized by ligation of the EcoRI sticky ends. This cloned HBV genome was digested with HaeII, which cuts in the 3' non-coding region. Recessed ends were filled in with Klenow and HindIII linkers were ligated. The DNA was cut with HindIII and subsequently with XbaI, which has a single site in the HBV coding region. A 1.2 kb XbaI-HindIII fragment containing 586 base pairs of the coding sequence of HBV and 607 base pairs of the 3' non-coding region was isolated by gel electrophoresis. This fragment was cloned into pHBS5-3 previously cut with XbaI and HindIII and treated with alkaline phosphatase, to yield pHBS5-Hae2-1.

pGAP-2 is a pBR322 derived vector which contains a BamHI insert that has the GAP coding sequence, 5' and 3' flanking regions. There are two XbaI sites in this plasmid: one in the coding region and one in the 3' flanking sequences. pGAP'$_2$ is a derivative of pGAP-2 in which the XbaI site present in the 3' flanking region has been eliminated. For this purpose, 50 μg of pGAP-2 were partially digested with XbaI, treated with Bal31 to remove 25 base pairs per end and ligated. The plasmids were used to transform HB101 and the transformants were selected for loss of the XbaI site in the 3' flanking region.

(ii) Plasmid pPYK-A (FIG. 1A):

This plasmid derived from pBR327, contains a 2.89 kb BamHI-ThaI fragment corresponding to the yeast PYK gene. The sequence of this DNA has been described by Burke et al., J. Biol. Chem. (1983) 258:2193-2201, and shown to contain 915 bp of promoter sequence, 470 bp of terminator sequences and the whole coding region. This fragment supplied by Burke was ligated to BamHI linkers, digested with BamHI and ligated to BamHI digested pBR327 to produce pPYK-A.

(c) Other plasmids used in the construction of yeast expression vectors.

The two plasmids described below were used only as a construction vehicle in the preparation of yeast expression vectors since they had convenient restriction sites.

(i) Plasmid pAV-4 (FIG. 4):

This plasmid is derived from pAV-1/TK-A (Luciw et al. Cell (1983) 33:705-716) which contains two long terminal repeat (LTR) sequences of Raus Sarcoma virus (RSV), the thymidine kinase gene of Herpes Simplex virus and pBR322 sequences containing the amp$^R$ gene. pAV-1/TK-A was digested with BamHI, diluted and self-ligated. After cloning in E. coli HB101 and selecting transformants with ampicillin, plasmid pAV-1 was obtained which had a deletion of the thymidine kinase gene. pAV-1 was subsequently digested with EcoRI. The recessed ends were filled in with Klenow and BamHI linkers were ligated to the blunt ends. After BamHI digestion, the plasmid was recircularized, cloned in HB101 and transformants were selected for amp$^R$. Plasmid pAV-4 which contains only U3 of the RSV-LTR sequences was thus obtained.

(ii) Plasmid pMV2ZRI (FIG. 1A):

This plasmid derived from pBR328 lacks EcoRI sites and contains two LTR from Harvey murine sarcoma virus (HaMSV). Preparation of pMV2ZRI was as follows. A 2.3 Kb HindIII-BamHI fragment from clone H-1 (Willumsen et al. J. Virol. (1984) 601-603) was cloned in HindIII-BamHI digested pBR328 to produce pV15-3LTR. This plasmid was digested with XbaI, which cuts once in the LTR sequence, and recircularized. After transformation of E. coli HB101 and selection of transformants with ampicillin, pV15-1LTR was obtained in which 2 LTR sequences have been deleted. After BamHI digestion of pV15-1LTR, the recessed ends were filled in with reverse transcriptase, the plasmid was recircularized and used to transform E. coli HB101. After selections of transformants with ampicillin, plasmid pV15-(Z-Bam) was obtained. This plasmid was digested with BalI, which cuts once in the insert (outside the LTR sequence) and once in pBR328, BamHI linkers were ligated to the blunt ends and the plasmid was recircularized and cloned in E. coli HB101 to produce pV15(Bal→H3). Plasmid pMV-2 was then prepared by joining three fragments: an EcoRI-HindIII vector fragment from pV15(Bal→H3) containing pBR328 sequences and one LTR sequence from HaMSV; a 346 bp HindIII-BamHI from pBR322; and a BamHI-EcoRI fragment from pV15-1LTR containing one LTR sequence from HaMSV. After ligation, the mixture was cloned in E. coli HB101 and selection of transformants was carried out with ampicillin. Plasmid pMV2 was digested with EcoRI, the recessed ends were filled in with Klenow and the plasmid was recircularized and cloned in HB101 to produce pMV2ZRI which lacks EcoRI sites.

b 2. Sequencing

Nucleotide sequencing was performed as described by Sanger and Coulson (1977) Proc. Nat. Acad. Sci. USA 74:5463-5467. Amino acid sequences were determined based on the nucleotide sequences.

3. Restriction Enzymes

The following restriction enzymes were employed in a high salt buffer (10X: 1.5 M NaCl, 100 mM MgCl$_2$, 100 mM Tris, pH 7.5): BamHI, XhoI, XbaI and SalI. EcoRI was employed in a medium salt buffer (10X: 500 mM NaCl, 100 mM MgCl$_2$, 100 mM Tris, pH 7.5). BalI was employed in a low salt buffer (10X: 100 mM NaCl, 100 mM MgCl$_2$, 100 mM Tris, pH 7.5). Restriction was accomplished with 2 units of restriction enzyme per µg DNA (25 µl total volume) at 37° C.

4. Construction of Plasmids

DNA fragments having cohesive ends were joined by annealing and ligating under the following conditions. One µg DNA in a total volume of 100 µl of buffer (10 mM Tris, pH 7.5, 10 mM MgCl$_2$, 2 mM ATP, 5 mM DTT, 1 µl Biolabs T4 ligase, approximately 400 units), was incubated at 4° C. for 4-6 hrs. DNA fragments having blunt ends were ligated under the same conditions but for 12 to 15 hrs. Recombinant plasmids were cloned as follows. The DNA (about 1 µg) was added to 100 µl of competent E. coli HB101 cells (1-2×10$^7$ cells/µl), and the mixture incubated at 4° C. for 20 min., at 37° C. for 2 min., and at room temperature for 15 min. To the mixture was then added 1 ml of L-broth, and the mixture was shaken for 60-90 min. at 37° C., followed by plating on L-agar under selective conditions.

5. Klenow Procedure for Restoring and Joining Blunt Ends

A reaction volume of 50 µl of a buffer (6 mM Tris, pH 7.5, 6 mM MgCl$_2$, 1 mM DTT, 50 mM NaCl) and 50 µM each of the four dNTP was incubated at 37° C. for 30 min. in the presence of 5 units of DNA polymerase I, and the reaction stopped by extracting with phenol/chloroform (1:1). For ligation of two blunt ends, the DNA was spun down, the pellet washed one time with ethanol, the pellet resuspended in 8.3 µl of water and 5 µl each of 20X Tris-MgCl$_2$, 20X ATP, 20X DTT, and 2 µl 100 mM spermidine added.

6. Preparation of Linkers

Linkers were prepared by the method of Beaucage and Caruthers (1981) Tetrahedron Lett. 22:1859-1862.

7. Plasmid Amplification and Isolation

One ml of an overnight saturated bacterial culture was added to 100 ml of an amplification medium (20X M9 mix, 5 ml; 10X M9 salts, 10 ml; L-broth, 10 ml; 1% B1, 0.1 ml; 20% CAA, 0.5 ml; 1% Leu, 1 ml; 1% Pro, 1 ml; 2% Amp/DMSO, 0.2 ml) and cells were grown to O.D.$_{650}$=1 in a 37° C.-airshaker (about 4 hr.). Ten ml L-broth; 0.5 ml 20% CAA and 1 ml of 50% glucose were then added and the cells grown for an additional 30 min. An aliquot of 0.5 ml of a freshly prepared solution of 50 mg/ml chloramphenicol in 100% ethanol was added to the mixture and the culture grown overnight.

The culture was spun down in a 250 ml Beckman centrifuge bottle, 4.5K rpm/20 min. in a Beckman J-6B. The pellet was suspended in 10 ml of 0.15 M NaCl, 50 mM Tris, pH 7.5 and centrifuged as described before. The pellet was resuspended in 1 ml G.E.T. (25 mM Tris, pH 8, 10 mM EDTA, 50 mM glucose), an additional 1 ml of G.E.T. containing 4 mg/ml of lysozyme was added, and the mixture cooled on ice for 45 min. Four ml of 0.2 N NaOH, 1% SDS, were added followed by gentle mixing and incubating on ice for 15 min. Three ml of 3 M potassium acetate, pH 4.8, were added and after cooling on ice for 1 hr, the mixture was spun at 10K rpm/20 min. in a Beckman J2-21 (rotor JS-13). The supernatant was diluted with an equal volume of isopropanol. The mixture was allowed to stand at room temperature for 5 min., followed by centrifugation at 10K rpm/20 min. The resulting pellet was suspended in 1 ml T.E., 5 µl RNAse A (10 mg/ml in 50 mM sodium acetate, pH 4.8; boiled 10 min.) added and the mixture allowed to stand at room temperature for 20 min. One-half volume of 30% PEG 8000/1.5 M NaCl was then added to the mixture and cooled on ice for 30 min., followed by centrifugation at 10K rpm/20 min. The pellet was redissolved in 0.4 ml T.E., transferred to a 1.5 ml microfuge tube and extracted two times with phenol/chloroform followed by one time chloroform. The aqueous phase was split into two 400 µl aliquots in two tubes and 3 volumes ethanol added to each. The alkanolic aqueous phases were mixed at which time a thread-like DNA precipitate occured. After spinning in a microfuge for 5min., the DNA was ethanol rinsed and dried in a Speedvac. The combined pellets were dissolved in water or TE, normally yielding about 0.3-1.0 mg.

8. Yeast Transformation

Saccharomyces carlsbergensis strain 2150-2-3, (Mat a, adel, leu2-04, cir°) obtained from Dr. Leland Hartwell, University of Washington, was used for transformation. The yeast cells were grown to an O.D.$_{650}$ of about 1 in non-selective medium (100 ml of cells provides about 0.5 ml of spheroplasts). These cells were pelleted in 150 ml sterile Corex bottles by centrifuging for 5 min. at 3K, followed by washing the resulting pellet with sterile distilled water and repeating centrifugation. The cells were resuspended in 0.05 vol of original culture in 1 M sorbitol with 15% glycerol, followed by freezing in dry ice-ethanol and storing at −70° C.

Spheroplasts were prepared by resuspending cells in 0.05 vol of the original culture volume using 1 M sorbitol, 50 mM potassium phosphate, pH 7.5 (SP). A 50 µl aliquot was diluted to 1 ml with 0.1% SDS and the initial O.D.$_{650}$ value was determined. The cell suspension was made 1 mM DTT followed by the addition of zymolase (10 mg/ml in SP) to provide a concentration of 0.1 mg/ml. The mixture was incubated at 30° C. with gentle shaking and monitored, with the reaction terminated when the O.D.$_{650}$ value was 10% of the original value (about 20-40 min.). The spheroplast mixture was then centrifuged for 3 min. at 5K, washed with 1 M sorbitol, centrifuged again, washed once with STC, centrifuged, resuspended and washed again. For transformation, approximately 100 µl of spheroplasts in 1xSTC and 50 µl of DNA in 1xSTC were combined and allowed to stand for 5 min. at room temperature, followed by addition of 1 ml 40% PEG4000, and the mixture allowed to stand for 10 min. at room temperature. Cells were pelleted (2.5 Krpm, 10 min.), resuspended in 2.5 ml YEPD-1 M sorbitol and allowed to express for 2 hr. at 30° C. with shaking. Cells were spun (2.5 Krpm, 10 min.) and resuspended in 100-500 µl of 1 M sorbitol. The mixture was then plated in selective top agar (10 ml) onto selective leu- plates.

9. Growth and Lysing of Yeast Clones

The yeast clone was inoculated into 2 ml of Leu⁻ minimal media, and the yeast cells allowed to grow at 30° C., with shaking for 24-48 hrs. until saturated. The cells were then pelleted in a microfuge for about 30 sec., the supernatant poured off and the pellet resuspended in 50 μl LSB. After boiling for 5 min., the cellular debris was removed by centrifugation for 1 min. in a microfuge and a 10 μl aliquot was run on an acrylamide gel.

10. Preparation of FeLV Virus

The cat cell line LU-1 (AK-D, lung cells, A.T.C.C. accession number CCL 150) chronically infected with FeLV-A, B or C, was grown to about one half confluency in 150 cm² tissue culture flasks. The culture media (DME-10%FCS) was collected and replaced with fresh media each day for the next three days. At the end of the collection, the cells were trypsinized, plated in new flasks at low density and the collection regime was repeated when the cells reached one half confluency. After about one liter of tissue culture media was collected, the media was clarified by centrifugation at 2,200 g for 20 min and the virus was pelleted by centrifugation at 28,000 g for 12 hours. The pellet was resuspended in 10 mM Tris, 100 mM NaCl, 1 mM EDTA and layered on top of a 15–50% sucrose gradient. The gradient was centrifuged at 40,000 rpm in a SW-41 rotor for 2 hours. The tubes were then removed and the visible virus band was aspirated with a syringe and needle. To confirm that this band corresponded to the virus, infected cells were labeled with ³H-uridine and the labeled virus was detected in the gradient by determining radioactivity in each fraction. Virus stocks prepared as described above were stored at 4° C. in the sucrose solution from the gradient.

11. Preparation of Anti-FeLV Antibodies

Virus prepared as outlined above was mixed with equal volumes of complete Freunds adjuvant and a stable emulsion was made by repeated passage through a hypodermic needle. Twenty to fifty μg of protein (determined by Coomassie blue binding assay) of each virus preparation was then injected intramuscularly into the hind quarters of rabbits. The rabbits were boosted at three week intervals with 20–50 μg of virus protein emulsified in incomplete Freunds adjuvant with intramuscular injections in the hind quarters. Rabbits were bled one week after each boost and viral antibody titers were determined by an ELISA assay against each purified virus.

12. Western Analysis

Transformed yeast cells or FeLV protein controls were electrophoresed on 10% polyacrylamide gels (Laemmli, Nature (1970) 277:680) and proteins were subsequently electroblotted onto nitrocellulose filters (Towbin, Staehlin, and Gordon, Proc. Natl. Acad. Sci. USA (1979) 76:3450). The filter was preincubated with goat serum and subsequently treated with rabbit anti-FeLV antiserum prepared as previously described (Section 11) or with mouse serum against envelope protein prepared as described in Results (Section 6). The filter was then incubated with a second goat anti-rabbit or goat anti-mouse antibody conjugated with horseradish peroxidase (Boehringer-Mannheim) and finally incubated with horseradish peroxide color development reagent (Bio-Rad) and washed.

Results

1. Sequences and Features of the FeLV Envelope Genes

The envelope gene of feline leukemia virus is located on the 3'-portion of the viral genome. Sequencing of the envelope gene region (including the leader sequence, gp70 and partial p15E) for each subgroup of FeLV was performed, and the results are presented in Appendix A. Asterisks indicate homology between corresponding bases in the sequence of each subgroup. Sequencing was carried out from the HindIII site located immediately to the right of the center of the viral genome in the pol region. For each subgroup, over 2.5 kbp of continuous sequence was determined. Significant homology was found among the three subgroups, as well as between the subgroups and several strains of murine leukemia virus (MuLV). The similarity to MuLV helped in identifying various functional regions in the FeLV genome.

The translational initiation codon (ATG) for all three subgroups is indicated on the sequence in Appendix A. Coding for the N-terminus of the gp70 envelope protein begins at a location 99 base pairs downstream from the initiation codon. All three subgroups have nearly identical leader peptides. The coding for the p15E envelope protein begins at a location 1350 base pairs downstream from the initiation codon in FeLV-B. For FeLV-C, the distance is 1281 base pairs, and for FeLV-A, the distance is 1290 base pairs.

The amino acid sequences for the envelope proteins from each viral subtype were determined and are set forth in Appendix B.

2. Preparation of pCP-envB-R or pCP-envA-R

A yeast expression vector derived from pCl/1 and carrying the FeLV-B gp70 gene and a portion of the p15E coding region was prepared as illustrated in FIGS. 1A-1B. The pyruvate kinase (PYK) promoter and terminator regions were obtained from plasmid pPYK-A (described under Materials and Methods, section 1.b.). Plasmid pPYK-A was completely digested with restriction enzymes XbaI and SalI gel purified to separate the resulting two fragments. The longer fragment carrying the Amp$^R$ gene was retained for use later, as will be described below. The shorter fragment carrying the pyruvate kinase gene (with the exception of the first four bases of the coding region) and terminator was inserted into a SalI/XbaI cut on plasmid pMV2ZRI (described under Materials and Methods, section 1.c.). Plasmid pMV2ZRI is free of EcoRI sites.

The resulting plasmid (pMV-PYK) included a single EcoRI site located 32 codons upstream of the termination codon of the pyruvate kinase gene. Plasmid pMV-PYK was digested with XbaI and EcoRI to remove most of the PYK coding region, and after gel purification, a linker was ligated in the resulting XbaI/EcoRI cut. The linker included cohesive ends for XbaI and EcoRI and provided a BalI restriction site (see FIG. 1A). The resulting plasmid (pMP-Linker) was completely digested with XbaI and SalI, and the shorter fragment carrying the BalI restriction site ligated to the larger XbaI/SalI fragment of plasmid pPYK-A obtained earlier. The resulting plasmid (pPYK-Linker) was identical to pPYK-A except that most of the pyruvate kinase gene had been removed and replaced by the synthetic linker which provides for a unique BalI site.

A portion of the FeLV-B envelope gene region (env) was derived from plasmid pKC125. Plasmid pKC125 (described in Materials and Methods, section 1.a.) carries the entire FeLV-B genome. This plasmid was digested with restriction enzyme XhoI to remove the gag and pol genes (FIG. 2). The resulting plasmid (pKC-ΔXho) thus carried the envelope gene region together with a pair of BalI restriction sites at locations near either end. See FIG. 3. The BalI site near the 5'-end cleaves between nucleotides 102 and 103 in the leader sequence. The BalI site near the 3'-end cleaves within the p15E gene, leaving the gp70 envelope protein gene intact.

Referring now to FIG. 1B, the BalI fragment carrying the gp70 gene was excised from pKC-ΔXho and inserted into the unique BalI site on pPYK-Linker, resulting in plasmid pPL-envB. Insertion of the BalI fragment provides a fusion in the correct reading frame with the codons left from the PYK gene and from the XbaI-EcoRI linker (described previously). Therefore, 4 extra codons are fused at the 5' end of the gp70 gene in the leader sequence region (to nucleotide 103) and 33 codons are fused at the 3' end of the BalI fragment in the p15E coding region. Plasmid pPL-envB was digested with BamHI to excise the fragment carrying the portion of the envelope gene under transcriptional control of the PYK promoter and terminator regions. The BamHI fragment was then inserted into the unique BamHI restriction site in yeast plasmid pCl/1, and the resulting plasmid (pCP-envB-R) selected based on loss of tetracycline resistance.

A procedure similar to that described above and depicted in FIG. 1B was followed for the construction of pCP-envA-R, a yeast expression vector for the envelope protein of FeLV-A. In this case, plasmid pFeA12ΔXS (described in Materials and Methods, Section 1.a.) was used, instead of pKC-ΔXho, to provide for the FeLV-A env gene.

3. Preparation of Plasmid pCG-envB-R

A second yeast expression vector was derived from plasmid pUH28 (described under Materials and Methods, Section 1.b.) carrying the HBsAg gene under the transcriptional control of the GAPDH promoter and terminator regions. Plasmid pUH28 was restricted with BamHI and the fragment carrying the promoter, terminator and HBsAg gene was isolated. The BamHI fragment was then inserted into the unique BamHI site on plasmid pAV-4 (described in Materials and Methods, Section 1.c), which plasmid was free from NcoI and SalI sites. After cloning the resulting plasmid (pUH2-8/AV4-B) in E. coli HB101, the major portion of the HBsAg gene was removed by digestion with NcoI and SalI.

A BalI fragment from pKC-ΔXho was obtained as described previously in reference to FIG. 2. The BalI fragment was then inserted into the NcoI/SalI cut in pUH28/AV4-P by the Klenow procedure described in Materials and Methods. Inserting the BalI fragment restores the SalI site on the resulting plasmid (pUAB-envB), and also restores a correct reading frame with the first 7 codons of the GAPDH 5'- coding region from pUH28. The NcoI/BalI junction was sequenced to verify the correct reading frame. After expansion in E. coli HB101, plasmid pUAB-envB was restricted with BamHI and the fragment carrying the GAPDH promoter and terminator and envelope gene was isolated. The BamHI fragment was then inserted into the unique BamHI site on plasmid pCl/1 to produce plasmid pCG-envB-R.

4. Expression in Yeast

Yeast was transformed with pCP-envA-R, pCP-envB-R or pCG-envB-R, as described in Materials and Methods. Transformed yeast were estimated to produce about 2–5% of an approximately 55 kdal polypeptide corresponding to the FeLV-A or FeLV-B envelope protein, based on the total yeast protein produced with both yeast vectors. These estimates were based on Coomassie blue staining of total yeast proteins separated on polyacrylamide gels.

A Western Blot analysis with antibodies (rabbit) specific to FeLV-A or FeLV-B viral particles was performed, as described in Materials and Methods. The analysis identified the expected approximately 55 kilodalton polypeptide, as well as an approximately 30 kilodalton polypeptide. Thus, it appears that some proteolysis of the 55 kilodalton protein occurs in the yeast. Preparation of extracts in the presence of protease inhibitors alleviated the degradation.

5. Purification of Envelope Protein from FeLV-A or FeLV-B Synthesized in Yeast

Yeast cells transformed with vectors pCP-envA-R, pCP-envB-R or pCG-envB-R were grown to an $O.D._{650}=3$. Cells were harvested (3K rpm, 10 min.), resuspended in an equal volume of 0.1M Tris-SO$_4$, pH 9.4, 10 mM DTT and incubated at 30° C. for 20 min. Cells were pelleted (3K rpm, 10 min.), resuspended in 5 volumes of 1 M sorbitol, 50 mM potassium phosphate buffer pH 7.5 and 0.01 volume of zymolyase (10 mg/ml) were added. The mixture was incubated and monitored with the reaction terminated when the $O.D._{650}$ value was 10% of the original value (about 30 to 40 min.). The spheroplasts were centrifuged at 3K rpm for 10 min. and washed with 5 volumes of 1 M sorbitol. This step was repeated. The final pellet was resuspended in 1 volume of 50 mM Tris (pH 8.0), 10 mM NaCl, 1 mM phenylmethylsulfonylfluoride (PMSF), 1 μg/ml pepstatin and incubated for 5 minutes on ice to provide lysis. The mixture was transferred to microfuge tubes and centrifuged for 15 minutes. The pellet was resuspended in an equal volume of 0.2% SDS, 1 mM PMSF, 1 μg/ml pepstatin. The mixture was incubated 10–12 hours at 4° C. and centrifuged for 15 minutes in the microfuge. The pellet obtained corresponds to approximately 70% pure envelope protein.

For large scale preparations (over 25 ml of packed cells of starting material) volumes are scaled up accordingly. Spheroplasting usually takes 1½–2 hours.

6. Production of Neutralizing Antibodies Against FeLV Envelope Protein in Mice

A pellet which contained 70% pure envelope protein was obtained as described above (Section 5). The envelope protein was solubilized from the pellet material by boiling in an equal volume of 0.2% SDS for 5 minutes. The insoluble material was removed by centrifuging in a microfuge for 5 minutes at 4° C. and the supernatant containing the envelope protein was stored at −20° C. until used for animal injections. Four mice were injected, each with 13 μg of the solubilized envelope protein. The envelope protein was mixed with an equal volume of complete Freunds adjuvant (CFA) and was injected half intraperitoneally and half subcutaneously. One control mouse was injected with 0.2% SDS mixed with CFA and administered as above. On day 14 the mice were boosted with the same protocol except that the adjuvant used was incomplete Freunds adjuvant (ICFA). On day 21 the mice were bled using the heart puncture technique. 50–200 μl of blood was obtained and immediately diluted 1:10 with PBS. Red blood cells were spun out at 3K rpm for 10 minutes. The supernatant corresponds to the serum diluted about 1:20.

To test the reactivity of the mouse sera to FeLV virus, ELISA assays were performed with the mouse sera against FeLV virus, prepared as described under Materials and Methods. FeLV virus was diluted in PBS to a concentration of 20 μg/ml and then sonicated 3 times for 20 seconds each time to disrupt the virus. Microtiter wells were then coated with 50 μl of the virus and incubated for 1 hour at room temperature. Wells were washed 4 times with 5% goat serum/PBS.

Mouse sera were serially diluted in 1% goat serum/PBS: dilutions ranged from 1:20 to 1:500,000. 50 μl of mouse serum was applied to each well and incubated 1 hour at room temperature. Wells were washed again with 1% goat serum/PBS. The second antibody, peroxidase conjugated goat anti-mouse (Boehringer-Mannheim), was diluted 1:200 in 1% goat serum/PBS. 50 μl of the second antibody was applied to each well and incubated for 1 hour at room temperature. Wells were then washed 5 times with PBS. 1 μl of 30% $H_2O_2$ was added to 5 ml of a solution of 1 mg/ml ABTS in 0.1 M citrate-phosphate buffer, pH4 (peroxidase color development reagent) and 50 μl of the mixture were added to each well. Color development was stopped by diluting into 450 or 950 μl of $H_2O$ and absorbance was measured at 414 nm. Alternatively color development was stopped by adding 50 μl of 5% SDS and samples were read in a microtiter dish photometer (Flow Labs Instruments). 50% titers, defined as the dilution of antibody that gives 50% of the maximal color development, were calculated from this data and are shown in Table 1 and Table 2.

50% titers were also determined for sera of mice boosted again on day 28 and bled on days 35 and 91. Results are shown in Table 1. Mice sera were also used in a western blot analysis (described in Materials and Methods) against envelope protein or against FeLV virus. All sera reacted with the envelope protein made in yeast and with the gp70 from virus. The control serum (mouse normal serum) was negative on the western.

Immunizations of mice using 6 μg of envelope protein gave equivalent antibody titers to those previously discussed receiving 13 μg.

The capability of the mouse sera to neutralize virus was measured using an immunofluorescence assay. Heat inactivated mouse sera at various dilutions were mixed with 10 μl of media from FeLV infected LU-1 cells (AK-D, lung cells, A.T.C.C. accession number CCL 150) and incubated 1 hour at 37°. The various sera mixtures were then plated on cat LU-1 cells seeded about one third confluent on tissue culture chamber slides. After incubating LU-1 cells at 37° for five days to allow for virus replication, the cells were washed, fixed with cold methanol and pre-incubated 1 hour in PBS containing 1% goat serum. The fixed cells were incubated for one hour at room temperature with rabbit anti-FeLV antiserum, prepared as described under Materials and Methods, diluted 1:100 in PBS—1% goat serum. The cells were then washed with PBS and incubated for 1 hour at room temperature with goat anti-rabbit antibody conjugated with fluorescein isothiocyanate (from Boehringer Mannheim) diluted 1:25 in PBS—1% goat serum. Both the rabbit anti-FeLV antiserum and the goat anti-rabbit antibody had been pre-absorbed against fixed, uninfected LU-1 cells to eliminate high fluorescence background. After further washing with PBS, the slides were mounted in PBS - glycerol (1:1) and observed under the fluorescence microscope. The number of fluorescent cells in 4 vertical passes of the microscope over the slide was recorded for each serum dilution. The titer listed in Table 1 indicates the serum dilution that reduced the number of fluorescent cells to one half of the maximum number.

7. Diagnostic assay for FeLV infection using yeast produced envelope protein.

Purified envelope protein synthesized by yeast cells was used in a diagnostic assay to detect antibodies against FeLV antigens present in sera of animals naturally or experimentally infected with virus, or immunized with purified envelope protein. For this purpose, a preparation containing 70% pure envelope protein was obtained as previously described (Section 5 of Results). This preparation, which has 200–700 μg of protein per ml in 0.2% SDS, was diluted in PBS to 20 μg/ml and used in an ELISA assay to detect cat or mouse antibodies present in sera from the animals. (Identical results were obtained with the antigen diluted to 2 μg/ml.) Microtiter wells were coated with 50 μl of the envelope protein solution and incubated for 1 hour at room temperature. Wells were washed 4 times with 5% goat serum/PBS. Sera from animals infected with virus or envelope protein were serially diluted in 1% goat serum PBS: dilutions ranged from 1:20 to 1:500,000. 50 μl of the test serum was applied to each well and incubated at room temperature for 1 hour. Wells were washed again with 1% goat serum/PBS. The second peroxidase conjugated antibody (goat anti-cat or goat anti-mouse, Boehringer-Mannheim) was diluted 1:200 in 1% goat serum/PBS. 50 μl were applied to each well and incubated for 1 hour at room temperature. Color development was carried out as described previously (Section 6, Results) and 50% titers were determined.

Results shown in Tables 3, 4, and 5 indicate that the purified envelope protein synthesized by yeast transformed cells can be used to detect antibodies against FeLV antigen present in sera of infected or immunized animals.

According to the subject invention, novel DNA constructs are provided for the expression in yeast of a polypeptide having immunological activity corresponding to that of naturally-occurring FeLV envelope glycoproteins Such polypeptides may find particular use as vaccines against FeLV in susceptible hosts.

Although the foregoing invention has been described in some detail by way of illustration and example for purposes of clarity of understanding, it will be obvious that certain changes and modifications may be practiced within the scope of the appended claims.

APPENDIX A

Nucleotide homology between Feline Leukemia Virus envelope gene of subgroups A, B and C in the region from HindIII in the polymerase gene to the 3'-terminus of the LTR. Asterisks (*) indicate homology between corresponding bases in the sequence of each subgroup. Colons indicate gaps that have been left in certain regions for purposes of alignment of the three sequences, to provide maximal homology. The translational initiation condon of the envelope protein (ATG) is boxed.

APPENDIX A

Nucleotide homology between Feline Leukemia Virus envelope gene of subgroups A, B and C in the region from HindIII in the polymerase gene to the 3'-terminus of the LTR. Asterisks (*) indicate homology between corresponding bases in the sequence of each subgroup. Colons indicate gaps that have been left in certain regions for purposes of alignment of the three sequences, to provide maximal homology. The translational initiation codon of the envelope protein (ATG) is boxed.

```
[C] AAGCTTACCCCGCCAAACATGAAACAGCAAAAGTTGTTGCCAAGAAACTCTTAGAAGAGATCTTTCCTCGTT
    ********************************** *************** ** ***** ** *
[A] AAGCTTACCCCGCCAAACATGAAACAGCAAAAGTTGTCGCCAAGAAACTCTTAGAAGAAATTTTTCCCCGCT
    ********************************** *************************************
[B] AAGCTTACCCCGCCAAACATGAAACAGCAAAAGTTGTTGCCAAGAAACTCTTAGAAGAAATTTTTCCCCGCT

ACGGGATCCCTCAGGTATTGGGTTCGGATAATGGACCCGCCTTTATCTCCCAGGTAAGTCAGTCTGTGGCCA
    ********** ********** ******* ******************************************
    ACGGGATCCCCCAGGTATTGGGTTCAGATAATGGACCCGCCTTTATCTCCCAGGTAAGTCAGTCTGTGGCCA
    ********** **********************************************************
    ACGGGATCCCGCAGGTATTGGGTTCAGATAATGGACCCGCCTTTATCTCCCAGGTAAGTCAGTCTGTGGCCA

CCCTACTGGGGATTAATTGGAAATTACATTGCGCATACCGACCCCAAAGTTCAGGTCAGGTAGAAAGAATGA
    ***************** ******* ******* **************************************
    CCCTACTGGGGATTAATTGGAAGTTACATTGTGCATACCGACCCCAAAGTTCAGGTCAGGTAGAAAGAATGA
    ************************************************************************
    CCCTACTGGGGATTAATTGGAAGTTACATTGTGCATACCGACCCCAAAGTTCAGGTCAGGTAGAAAGAATGA

ATAGATCAATTAAGGAGACTTTAACTAAATTAACGCTAGAAACTGGCTCTAAGGATTGGGTACTCCTCTTGC
    ************************************************************ ****** ***
    ATAGATCAATTAAGGAGACTTTAACTAAATTAACGCTAGAAACTGGCTCTAAGGATTGGGTGCTCCTCCTGC
    ************************************************************************
    ATAGATCAATTAAGGAGACTTTAACTAAATTAACGCTAGAAACTGGCTCTAAGGATTGGGTGCTCCTCCTGC

CTTTGGTTTTATACCGGGTACGAAATACACCAGGTCCCCACGGGTTAACCCCTTTTGAAATCCTGTACGGGG
    *  **************** **  ** ** ************ ** ***************************
    CCCTGGTTTTATACCGGGTACGTAACACGCCGGGTCCCCACGGGTTAACTCCTTTTGAAATCCTGTACGGGG
    ************************ * *********************************************
    CCCTGGTTTTATACCGGGTACGTAACACGCCAGGCCCCCACGGGTTAACTCCTTTTGAAATCCTGTACGGGG

CACCCCCACCTCTGGCTCACTTTTTCGATGCTGACATCTCTAGCTTTGCTACCTCCCCACTATGCAGGCAC
    ********** ********  ** ********  ******** *****************************
    CACCCCCACCTATGGCTCACTTCTTTGATGCTGATATCTCTAGCTTCGCTACCTCCCCACTATGCAGGCAC
    *********** ***********  *******  *  ** * ******************************
    CACCCCCACCTATGGCTCACTTCTTTGATACTGATATCTCTCGTATCGCTACCTCCCCACTATGCAGGCAC

ATTTACGCGCCCTGCAGCTGGTCCAAGAAGAGATCCAGAGACCTCTAGCGGCAGCCTACCGAGAAAGGCTCC
    ***************** *********************  *********** ***  *****  ****
    ATTTACGCGCCCTGCAGCTGGTCCAAGAAGAGATCCGGAGACCTCTAGCGGCGGCCTACCAAGAAAAGCTCG
    ***************** ************************************** ***************
    ATTTACGCGCCCTGCAGCTGGTCCAAGAAGAGATCCAGAGACCTCTAGCGGCGGCCTACCGAGAAAAGCTCG

AAACCCCGGTTGTGCCTCACCCCTTCAAACCAGGAGACTCCGTCTGGGTGCGGAGACATCAAACCAAGAACC
    ************************************************** *  ******************
    AAACCCCGGTTGTGCCTCACCCCTTCAAACCAGGAGACTCCGTCTGGGTTCGGAGACATCAAACCAAGAACC
    ************************************************************************
    AAACCCCGGTTGTGCCTCACCCCTTCAAACCAGGAGACTCCGTCTGGGTTCGGAGACATCAAACCAAGAACC

TCGAGCCACGGTGGAAAGGACCACATATCGTCCTCCTGACCACCCCCACAGCCTTAAAGGTAGACGGAGTTG
    ***** ******************************************************************
    TCGAGCCACGGTGGAAAGGACCACATATCGTCCTCCTGACCACCCCCACAGCCTTAAAGGTAGACGGAGTTG
    *** ********************************************************************
    TCGAGCCACGGTGGAAAGGACCACATATCGTCCTCCTGACCACCCCCACAGCCTTAAAGGTAGACGGAGTTG

CTGCTTGGATTCACGCCTCCCACGTGAAAGCTGCAGGACCAACCACCGATCAGGACCTCCCGAACGACCCTA
    **** *  *******  *********************** **** ******  ** **  ***  *** *
    CTGCCTGGATTCACGCCTCTCACGTGAAAGCTGCAGGACCAACCACCAATCAAGACCTCTCGGACAGCCCCA
    ************************************************************************
    CTGCCTGGATTCACGCCTCTCACGTGAAAGCTGCAGGACCAACCACCAATCAAGACCTCTCGGACAGCCCCA

GCTCAGACGATCCATCAAG|ATG|GAAAGTCCAACGCACCCAAAACCCTCTAAAGATAAGACTTTCCCGTGGAA
    *******************|***|****************************************  ******
    GCTCAGACGATCCATCAAG|ATG|GAAAGTCCAACGCACCCAAAACCCTCTAAAGATAAGACTCTCTCGTGGAA
    *******************|***|****************************************************
    GCTCAGACGATCCATCAAG|ATG|GAAAGTCCAACGCACCCAAAACCCTCTAAAGATAAGACTCTCTCGTGGAA
```

```
CTTAGTGTTTCTGGTGGGGATCTTATTCCAAATAGATATGGGAATGGCCAATCCTAGCCCACACCAAGTATA
*****  ** *****************     * ****************** **  ****** *  ****
CTTAGCGTTTCTGGTGGGGATCTTATTTACAATAGACATAGGAATGGCCAATCCTAGTCCACACCAAATATA
*****  ********************  ******** ************************* ***  **
CTTAGTGTTTCTGGTGGGGATCTTATTCACAATAGACATAGGAATGGCCAATCCTAGTCCGCACCAAGTGTA

TAATGTAACTTGGGTAATAACCAATGTACAAACCAACTCCCGAGCTAATGCCACTTCTATGTTAGGAACCTT
***********************      *** *** ** *** *****  ***** ***************
TAATGTAACTTGGGTAATAACCAATGTACAAACTAACACCCAAGCTAACGCCACCTCTATGTTAGGAACCTT
************ *********** * ****  ** * ***** ******** ***** *******    *
TAATGTAACTTGGACAATAACCAACCTTGTAACTGGAACAAAGGCTAATGCCACCTCCATGTTGGGAACCCT

AACCGATGCCTACCCTACCCTATATGTTGATTTATGTGACCTAGTGGGAGACACCTGGGAACCTATAGCCCC
********************  *  * **** ** ******************************** ** 
AACCGATGCCTACCCTACCCTACATGTTGACTTATGTGACCTAGTGGGAGACACCTGGGAACCTATAGTCCT
** ** ****  *******   **  ************  **  * ** *** * ***  * *  ** *  
GACAGACGCCTTCCCTACCATGTATTTTGACTTATGTGATATAATAGGAAATACATGGAACCCTTCAGATCA

AGACCCA::::::::::AGATCTTGGGCACGTTATTCCTCCTCAACACATGGATGCAAAACTACAGATAGAAA
* *****           **********   ******** * ****** ***** ***** **********
AAACCCAACCAATGTAAAACACGGGGCACGTTACTCCTCCTCAAAATATGGATGTAAAACTACAGATAGAAA
* ***                            * **  * ********* *  *   **    *    * 
GGAACCA:::::::::::::::::::::::::::TTCCCAGGGTATGGATGTGATCAGCCTATGAGGAG

AAAACAGCAACAAACATACCCCTTTTATGTCTGCCCAGGGCATGCCCCCTCGATGGGGCCTAAGGGAACATA
*************** **************  ******* ********* **  ***** *********
AAAACAGCAACAGACATACCCCTTTTACGTCTGCCCCGGACATGCCCCCTCGTTGGGGCCAAAGGGAACACA
** **  *    * **********  * ******** **********       *  ****  *  ** **
GTGGCAACAGAGAAACACAGCCTTTTATGTCTGTCCAGGACATGCC::::::::::::::::AACCGGAAGCA

TTGTGGAGGGGCACAAGATGGGTTTTTGTGCCGCATGGGGATGTGAAACCACCGGAGAGGCTTGGTGGAAGCC
**************************************************************************
TTGTGGAGGGGCACAAGATGGGTTTTTGTGCCGCATGGGGATGTGAGACCACCGGAGAAGCTTGGTGGAAGCC
***** **  *****************  **  ***** * * *  ********    *** ** *****
ATGTGGGGGCCACAAGATGGTTCTGCGCTGTATGGGGTTGCGAGACCACCGGGGAAACCTATTGGAGACC

CACCTCCTCATGGGACTATATCACAGTAAAAAGAGGAAGTAATCAG::::::::::::::::::::::::::::
**********************************     * ****
CACCTCCTCATGGGACTATATCACAGTAAAAAGAGGGAGTAGTCAG::::::::::::::::::::::::::::
************************** **  ***  ** ***
CACCTCCTCATGGGACTACATCACAGTAAAAAAAGGGGTTACTCAGGGAATATATCAATGTAGTGGAGGTGG

:::::::::::::::::::::::::::::::::::::::::::::::::GACAATAGCTGTAAGGGCAAATGTAA
                                                 **************  ****  **
:::::::::::::::::::::::::::::::::::::::::::::::::GACAATAGCTGTGAGGGAAAATGCAA
                                                    *   *   *  *   *   *
TTGGTGTGGGCCCTGTTACGATAAAGCTGTTCACTCCTCGACAACGGGAGCTAGTGAAGGGGGCCGGTGCAA

CCCCCTGGTCTTGCAGTTCACCCAGAAGGGAAGACAAGCCTCTTGGGACAGACCTAAAATGTGGGGGCTACG
**********  ********************************** *** ***  *  *******   **
CCCCCTGGTTTTGCAGTTCACCCAGAAGGGAAGACAAGCCTCTTGGGACGGACCTAAGATGTGGGGATTGCG
**** ** * *****  * *************************** * *** **  **   *     * *
CCCCCTTGATCTTGCAATTTACCCAAAAGGGAAGACAAACATCTTGGGATGGACCTAAGTCATGGGGGCTACG

ACTATACCGTTCAGGATATGACCCTATAGCCCTGTTCTCGGTATCCCGGCAAGTAATGACCATTACGCCGCC
**********  ****************** *  *** **** **  ***** *** **************
AGTATACCGTACAGGATATGACCCTATCGCTTTATTCACGGTGTCCCGGCAGGTATCAACCATTACGCCGCC
**********  ***************  *    *** ****  ****** * **** **************
ACTATACCGTTCAGGATATGACCCTATAGCCCTGTTCTCGGTATCCCGGCAAGTAATGACCATTACGCCGCC

TCAGGCGATGGGACCCAACTTAGTCTTACCTGATCAAAAACCCCCATCCCGACAATCTCAAACAAAGTCCAA
***  *  ********  *** ****************************** ************ ******
TCAGGCAATGGGACCAAACCTAGTCTTACCTGATCAAAAACCCCCATCCCGACAATCTCAAACAGGGTCCAA
******  ******* *****  *  *****************   * ****** ***********  ****
TCAGGCCATGGGACCAAATCTAGTCCTGCCTGATCAAAAACCCCCATCCAGGCAATCTCAAATAGAGTCCCG

GGTGACAACCCAGAGGCCCCAAATAACTAGCAGCACCCCAAGG::::::::::::::::::::TCTGTCGCCTC
 ***  ************* ****  * *  * ********                     *****  ** *
AGTGGCGACCCAGAGGCCCCAAACGAATGAAAGCGCCCCAAGG::::::::::::::::::::TCTGTTGCCCC
 **  *  *  **          *****  * * *  *****
AGTAACACCTCACCATTCCCAAGGCAACGGAGGCACCCCAGGTATAACTCTTGTTAATGCCTCCATTGCCCC

C:::::::::::::::GCTACCATGGGTCCCAAACGGATAGGGACCGGAGATAGATTAATAAAATTTAGTGCA
*               * **** *********** *********  *  *  *    ***********   **
C:::::::::::::::ACCACCATGGGTCCCAAACGGATTAGGACCGGAGATAGGTTAATAAAATTTAGTACA
                  *** **********************   ***************** ********
TCTAAGTACCCCTGTCACCCCCGCAAGTCCCAAACGGATTGGGACCGGAGATAGGTTAATAAAATTTAGTACA

AGGGACATACCTAGCCTTAAATGCCACCGACCCCAACAAAACTAAAGACTGTTGGCTCTGCCTGGTTTCTCG
*****************************************************************   ******
AGGGACATACCTAGCCTTAAATGCCACCGACCCCAACAAAACTAAAGACTGTTGGCTCTGCCTGGTTTCTCG
*************************** *********    ********   ***************   **
AGGGACATACCTAGCCTTAAATGCCACCGACCCCAACAGAACTAAACACTGTTGGCTCTGCCTGGTTTCTCG

ACCACCTTATTACGAAGGGATTGCAGTCTTAGGTAACTACAGCAACCAAACAAACCCCCCCCCATCCTGCCT
******  ********************** ******************************* ***********
ACCACCCTATTACGAAGGGATTGCAATCTTAGGTAACTACAGCAACCAAACAAACCCCCCCCATCCTGCCT
************************************************************************
ACCACCCTATTACGAAGGGATTGCAATCTTAGGTAACTACAGCAACCAAACAAACCCCCCCCATCCTGCCT

ATCTACCCCGCAACATAAACTGACTATATCAGAAGTGTCCGGGCAAGGTTTGTGCATAGGGACTGTTCCTAA
****  ***  *****  *****  **** ** ***** *******  ***********************
ATCTATTCCGCAACACAAACTAACCATATCTGAAGTATCAGGGCAAGGACTGTGCATAGGGACTGTTCCTAA
******************************** ********************************* ******
ATCTATTCCGCAACACAAACTAACCATATCTGAAGTATCAGGGCAAGGACTGTGCATAGGGACTGTTCCTAA
```

```
GACCCACCAAGCTTTGTGCAAAAAGACACAAAAAGGACATAAAGGGACTCACTACCTGGCAGCCCCCAACGG
********* ********  ******* * ******* **** * ***** ** ** **********
GACCCACCAGGCTTTGTGCAATGAGACACAACAGGGACATACAGGGGCGCACTATCTAGCCGCCCCCAACGG
**************************************************************** **
GACCCACCAGGCTTTGTGCAATGAGACACAACAGGGACATACAGGGGCGCACTATCTAGCCGCCCCCAATGG

CACCTATTGGGCCTGTAACACTGGACTCACCCCATGCATTTCCATGGCAGTGCTCAATTGGACCTCTGATTT
*********************************************** ********************
CACCTATTGGGCCTGTAACACTGGACTCACCCCATGCATTTCCATGGCGGTGCTCAATTGGACCTCTGATTT
***********************************  ********* **********************
CACCTATTGGGCCTGTAACACTGGACTCACCCCATGTATTTCCATGGCGGTGCTCAATTGGACCTCTGATTT

TTGTGTCTTAATCGAATTATGGCCCAGAGTAACCTACCATCAACCCGAATATATTTACACACATTTCGACAA
***************************** ** ************** *********  * * ***
TTGTGTCTTAATCGAATTATGGCCCAGAGTGACTTACCATCAACCCGAATATGTGTACACACATTTTGCCAA
**********************************************************************
TTGTGTCTTAATCGAATTATGGCCCAGAGTGACTTACCATCAACCCGAATATGTGTACACACATTTTGCCAA

AGCTGTCAGGTTCCGAAGAGAACCTATATCACTAACCGTTGCCCTTATGTTGGGAGGACTCACCGTAGGGGG
** ****** ************** ********* ******************** ****** **  ****
AGCTGTCAGGTTCCGAAGAGAACCAATATCACTAACGGTTGCCCTTATGTTGGGAGGACTTACTGTAGGGGG
****  ********************************************************** ******
AGCTGGCAGGTTCCGAAGAGAACCAATATCACTAACTGTTGCCGTCATGTTGGGAGGACTCACTGTAGGGGG

CATAGCCGCGGGGGTCGGAACAGGGACTAAAGCCCTCCTTGAAACAGCCCAGTTCAGACAACTACAAATAGC
*****************************************************************  **
CATAGCCGCGGGGGTCGGAACAGGGACTAAAGCCCTCCTTGAAACAGCCCAGTTCAGACAACTACAAATGGC
**********************************  **********************************
CATAGCCGCGGGGGTCGGAACAGGGACTAAAGCCCTCATTGAAACAGCCCAGTTCAGACAACTACAAATGGC

CATGCACACAGACATCCAGGCCCTGGAAGAGTCAATTAGTGCCTTAGAAAAATCCCTGACCTCCCTCTCTGA
***************************  *****  ***************** *************  ***
CATGCACACAGACATCCAGGCCCTAGAAGAATCAATTAGTGCCTTAGAAAAGTCCCTGACCTCCCTTTCTGA
**********************************************************************
CATGCACACAGACATCCAGGCCCTAGAAGAGTCAATTAGTGCCTTAGAAAAGTCCCTGACCTCCCTTTCTGA

GGTAGTCCTACACAATAGGCGGGGCCTAGATATTCTGTTCTTACAAGAGGGAGGGCTCTGTGCCGCATTAAA
 ******  ****  ** ************** ********************************** **
AGTAGTCTTACAAAACAGACGGGGCCTAGATATTCTATTCTTACAAGAGGGAGGGCTCTGTGCCGCATTGAA
**************************** ****************************************  **
AGTAGTCTTACAAAACAGACGGGGCCTGGATATTCTATTCTTACAAGAGGGAGGGCTCTGTGCCGCATTAAA

AGAAGAATGCTGCTTCTATGCAGATCACACCGGACTCGTCCGAGACAATATGGCTAAATTAAGAGAAAGACT
********** ***********  **********************************************
AGAAGAATGTTGCTTCTATGCGGATCACACCGGACTCGTCCGAGACAATATGGCTAAATTAAGAGAAAGACT
************************************** *******************************
AGAAGAATGTTGCTTCTATGCGGATCACACCGGACTTGTCCGAGACAATATGGCTAAATTAAGAGAAAGACT

AAAACAGCGGCAACAACTGTTTGATTCCCAACAGGGATGGTTTGAAGGATGGTTCAACAAGTCCCCCTGGTT
************************ * *******************************************
AAAACAGCGGCAACAACTGTTTGACTCCCAACAGGGATGGTTTGAAGGATGGTTCAACAAGTCCCCCTGGTT
*********************************  ************************************
AAAACAGCGGCAACAACTGTTTGACTCCCAACACGGATGGTTTGAAGGATGGTTCAACAAGTCCCCCTGGTT

TACAACCCTAATTTCCTCCATCATGGGCCCCTTACTAATCCTACTCCTAATTCTCCTCCTCGGCCCATGCAT
********************* ***************************************  *********
TACAACCCTAATTTCCTCCATTATGGGCCCCTTACTAATCCTACTCCTAATTCTCCTCTTCGGCCCATGCAT
**********************************************************************
TACAACCCTAATTTCCTCCATTATGGGCCCCTTACTAATCCTACTCCTAATTCTCCTCTTCGGCCCATGCAT

CCTTAACCGATTAGTGCAATTCGTAAAAGACAGAATATCTGTGGTACAAGCCTTAATTTTAACCCAACAGTA
*********  ** ****************************************** *************
CCTTAACCGATTAGTACAATTCGTAAAAGACAGAATATCTGTGGTACAGGCTTTAATTTTAACCCAACAGTA
*******  *************************************** *********************
CCTTAACAGATTAGTACAATTCGTAAAAGACAGAATATCTGTGGTACAAGCCTTAATTTTAACCCAACAGTA

CCGACAGATACAACAATACGATTCGGACCGACCATGATTTCCAATTAAATGTATGATTCCATTTAGTCCCTA
** *******  * ********** ****************************************** ***
CCAACAGATAAAGCAATACGATCCGGACCGACCATGATTTCCAATTAAATGTATGATTCCATTTAGTCCCCA
*****************************************  ***************************
CCAACAGATAAAGCAATACGATCCGGACCGACCATAATTTCCAATTAAATGTATGATTCCATTTAGTCTCCA

GAAGAAGGGGGAAATGAAAGACCCCCCCCCCACCCCAAAACTTAGCCAGCTACTGCAGCAATGCCATTTCA
***  ******* * ****  **     ******** **********************  **  ******
GAAAAAGGGGGGATGAAAGACCCCCT:::::ACCCCAAAATTTAGCCAGCTACTGCAGTGGTGTCATTTCA
*************  **************  ****************** **  *******  *******
GAAAAAGGGGGAATGAAAGACCCCCT::::ACCCCAAAATTTAGCCAGCTATTGCAGTGGTGCCATTTCA

CAAGGAATGGAAAATTACCCAAACATGTTCCCATGAGATATAAGGAAGTTAGGGGCTAAAACAGGATATCTG
****  ************  **   ************************************  ********
CAAGGCATGGAAAATTACTCAAGTATGTTCCCATGAGATATAAGGAAGTTAGAGGCTAAAACAGGATATCTG
************************ *************************** *****  **********
CAAGGCATGGAAAATTACTCAAGTATGTTCCCATGAGATACAAGGAAGTTAGAGGCTGAAACAGGATATCTG

TGGTTAAGCACCTGGGCCCCGGCTTAAAGCCAAGAACAGTTAAGCCTCGGATATAGCTGAAACAGCAGAAGT
***********************  ************** *** ****  *** **************** *
TGGTTAAGCACCTGGGCCCCGGCTTGAGGCCAAGAACAGTTAAACCCCGGATATAGCTGAAACAGCAGAAGT
****************************** **************  ************************
TGGTTAAGCACCTGGGCCCCGGCTTGAGGCCAAGAACAGTTAAACCCCC:ATATAGCTGAAACAGCAGAAGT

TTCAAGGCCACTGCCAGCAGTCTCCAGGCTCCCCAGTTGACCAGAGTTCAACCTTCCGCCTCATTTAAACTA
********* ************************************ **********************
TTCAAGGCCGCTGCCAGCAGTCTCCAGGCTCCCCAGTTGACCAGAGTTCGACCTTCCGCCTCATTTAAACTA
**************************************************************  ****
TTCAAGGCCGCTGCCAGCAGTCTCCAGGCTCCCCAGTTGACCAGAGTTCGACCTTCCGCCTCATTTGAACTA
```

```
ACCAATCCCCACGCTTCTCGCTTCTGTACGCGCGCTTTCTGCTATAAAATGAGCCATCAGCCCCCACCGGGC
**************** ************ ***********************  ****************  *****
ACCAATCCCCACGCCTCTCGCTTCTGTGCGCGCGCTTTCTGCTATAAAACGAGCCATCAGCCCCCAACGGGC
**************** ***************************************** **************
ACCAATCCCCACGCCTCTCGCTTCTGTGCGCGCGCTTTCTGCTATAAAACGAGCCCTCAGCCCCCAACGGGC

GCGCAAGTCTTTGCTGAGACTTGACCGCCCCGGGTACCCGTGTACCGAATAAACCTCTTGCTGTTTGCATCT
*********************************************** ***************  ********
GCGCAAGTCTTTGCTGAGACTTGACCGCCCCGGGTACCCGTGTAGCGAATAAACCTCTTGCTGATTGCATCT
********************************************* * ***************  ********
GCGCAAGTCTTTGCTGAGACTTGACCGCCCCGGGTACCCGTGTA:CGAATAAACCTCTTGCTGTTTGCATCT

GACTCGTGGTCTCGGTGTTCCGTGGGCACGGGGTCTCATCGCCGAGGAAGACCTAGTTCGGGGGTCTTTCA
**** ***************************** ********************************
GACTTGTGGTCTCGGTGTTCCGTGGGCACGGGGTCTCATCGCCGAGGAAGACCTAGTTCGGGGGTCTTTCA
**** *****************************************************************
GACTCGTGGTCTCGGTGTTCCGTGGGTACGGGGTCTCATCGCCGAGGAAGACCTAGTTCGGGGGTCTTTCA
```

APPENDIX B

Protein sequence homology between Feline Leukemia envelope protein of subgroups A, B and C. Amino acids are indicated using the one letter code. Asterisks indicate homology between corresponding amino acids in each subgroup. "XXXXXXXX" indicate gaps that have been left in certain regions for purposes of alignment of the three amino acid sequences to provide maximal homology.

```
[C]  MESPTHPKPSKDKTFPWNLVFLVGILFQIDMGMANPSPHQVYNVTWVITNVQTNSRANAT
     ***************- *** *******  **-*********|************-****
[A]  MESPTHPKPSKDKTLSWNLAFLVGILFTIDIGMANPSPHQIYNVTWVITNVQTNTQANAT
     ****************|***************** *********- *  ******
[B]  MESPTHPKPSKDKTLSWNLVFLVGILFTIDIGMANPSPHQVYNVTWTITNLVTGTKANAT

[C]  SMLGTLTDAYPTLYVDLCDLVGDTWEPIAPDPXXXRSWARYSSSTHGCKTTDRKKQQQTY
     ************|***********-  *    ****** *****************
[A]  SMLGTLTDAYPTLHVDLCDLVGDTWEPIVLNPTNVKHGARYSSSKYGCKTTDRKKQQQTY
     *********--*-|-****--* ** *             ****  *- ***
[B]  SMLGTLTDAFPTMYFDLCDIIGNTWNPSDXXXXXXXXXXQEPFPGYGCDQPMRRWQQRNT

[C]  PFYVCPGHAPSMGPKGTYCGGAQDGFCAAWGCETTGEAWWKPTSSWDYITVKRGSNQXXX
     ***********-***** ****************************************  *
[A]  PFYVCPGHAPSLGPKGTHCGGAQDGFCAAWGCETTGEAWWKPTSSWDYITVKRGSSQXXX
     *********    *** -* ******-******** ******  -*************** -*
     PFYVCPGHAXXXXXNRKQCGGPQDGFCAVWGCETTGETYWRPTSSWDYITVKKGVTQGIY

[C]  XXXXXXXXXXXXXXXXXXXXXDNSCKGKCNPLVLQFTQKGRQASWDRPKMWGLRLYRSGY
                         ****  ************* *********** **********+**
[A]  XXXXXXXXXXXXXXXXXXXXXDNSCEGKCNPLVLQFTQKGRQASWDGPKMWGLRLYRTGY
                         * *-****-********** ****** *******-**
[B]  QCSGGGWCGPCYDKAVHSSTTGASEGGRCNPLILQFTQKGRQTSWDGPKSWGLRLYRSGY

[C]  DPIALFSVSRQVMTITPPQAMGPNLVLPDQKPPSRQSQTKSKYTTQRPQITSSTPRXXXX
     ******-******+*********************** ***|*****   *|**
[A]  DPIALFTVSRQVSTITPPQAMGPNLVLPDQKPPSRQSQTGSKVATQRPQTNESAPRXXXX
     ******-*****+******************************  *-*|  - * *   *
[B]  DPIALFSVSRQVMTITPPQAMGPNLVLPDQKPPSRQSQIESRVTPHHSQGNGGTPGITLV

[C]  XXSVASXXXXXATMGPKRIGTGDRLINLVQGTYLALNATDPNKTKDCWLCLVSRPPYYEG
     ***          *************************-*****************
[A]  XXSVAPXXXXXTTMGPKRIGTGDRLINLVQGTYLALNATDPNRTKDCWLCLVSRPPYYEG
     *-**          * -  *********************************  ************
[B]  NASIAPLSTPVTPASPKRIGTGDRLINLVQGTYLALNATDPNRTKHCWLCLVSRPPYYEG

[C]  IAVLGNYSNQTNPPPSCLSTPQHKLTISEVSGQGLCIGTVPKTHQALCKKTQKGHKGTHY
     **-*************** ********************************  ** *  * **
[A]  IAILGNYSNQTNPPPSCLSIPQHKLTISEVSGQGLCIGTVPKTHQALCNETQQGHTGAHY
     ************************************************************
[B]  IAILGNYSNQTNPPPSCLSIPQHKLTISEVSGQGLCIGTVPKTHQALCNETQQGHTGAHY
```

```
[C]   LAAPNGTYWACNTGLTPCISMAVLNWTSDFCVLIELWPRVTYHQPEYIYTHFDKAVRFRR
      ***********************************************-**** *******
[A]   LAAPNGTYWACNTGLTPCISMAVLNWTSDFCVLIELWPRVTYHQPEYVYTHFAKAVRFRR
      ************************************************************
[B]   LAAPNGTYWACNTGLTPCISMAVLNWTSDFCVLIELWPRVTYHQPEYVYTHFAKAARFRR

[C]   EPISLTVALMLGGLTVGGIAAGVGTGTKALLETAQFRQLQIAMHTDIQALEESISALEKS
      ****************************************-*******************
[A]   EPISLTVALMLGGLTVGGIAAGVGTGTKALLETAQFRQLQMAMHTDIQALEESISALEKS
      *******************************-****************************
[B]   EPISLTVALMLGGLTVGGIAAGVGTGTKALIETAQFRQLQMAMHTDIQALEESISALEKS

[C]   LTSLSEVVLHNRRGLDILFLQEGGLCAALKEECCFYADHTGLVRDNMAKLRERLKQRQQL
      ************************************************************
[A]   LTSLSEVVLQNRRGLDILFLQEGGLCAALKEECCFYADHTGLVRDNMAKLRERLKQRQQL
      ************************************************************
[B]   LTSLSEVVLQNRRGLDILFLQEGGLCAALKEECCFYADHTGLVRDNMAKLRERLKQRQQL

[C]   FDSQQGWFEGWFNKSPWFTTLISSIMGPLLILLLILLLGPCILNRLVQFVKDRISVVQAL
      ************************************************************
[A]   FDSQQGWFEGWFNKSPWFTTLISSIMGPLLILLLILLFGPCILNRLVQFVKDRISVVQAL
      **** *******************************************************
[B]   FDSQHGWFEGWFNKSPWFTTLISSIMGPLLILLLILLFGPCILNRLVQFVKDRISVVQAL

[C]   ILTQQYQQIKQYDPDRP
      *****************
[A]   ILTQQYQQIKQYDPDRP
      *****************
[B]   ILTQQYRQIQQYDSDRP
```

APPENDIX B

Protein sequence homology between Feline Leukemia envelope protein of subgroups A, B and C. Amino acids are indicated using the one letter code. Asterisks indicate homology between corresponding amino acids in each subgroups. "XXXXXXXXX" indicate gaps that have been left in certain regions for purposes of alignment of the three amino acid sequences to provide maximal homology.

What is claimed is:

1. A polypeptide capable of inducing an immune response to produce antibodies specific for feline leukemia virus (FeLV) envelope glycoprotein, said polypeptide having been produced in a unicellular microorganism host and having the glycosylation pattern imposed by said unicellular host.

2. The polypeptide of claim 1, wherein said polypeptide is produced by a microorganism having the identifying characteristics of *Saccharomyces carlsbergensis* strain 2150-2-3 (pCP-envB-R) or *Saccharomyces carlsbergensis* strain 2150-2-3 (pCP-envA-R).

3. A polypeptide as in claim 1, wherein the microorganism host is a yeast.

4. A polypeptide as in claim 3, wherein the yeast is *Saccharomyces carlsbergensis*.

5. A polypeptide as in claim 1, having the immunological activity of at least one epitope of the FeLV pg70 glycoprotein.

6. A polypeptide as in claim 5, having the immunological activity of FeLV-B gp70.

7. A polypeptide as in claim 5, having the immunological activity of FeLV-A gp70.

8. A polypeptide as in claim 5, having the immunological activity of FeLV-C gp70.

9. A composition useful for vaccinating a feline host against FeLV, said composition comprising a polypeptide as in claim 1 in a physiologically acceptable medium, said polypeptide being present in an effective amount to induce an immunological response in said feline host.

10. A method for vaccinating a feline host against FeLV, said method comprising inoculating said host with the composition of claim 9.

11. A composition according to claim 9 wherein said composition comprises a mixture of at least two polypeptides each having an epitope of a different FeLV envelope glycoprotein.

12. A method for vaccinating a feline host against FeLV, said method comprising inoculating said host with the composition of claim 11.

13. FeLV envelope glycoprotein isolated from yeast transformed with a DNA construct comprising a DNA fragment coding for the amino acid sequence of at least one epitope of a feline leukemia virus (FeLV) envelope glycoprotein under transcriptional control of promoter and terminator signals recognized by yeast, and a replication system recognized by yeast.

* * * * *